United States Patent [19]

Urry

[11] Patent Number: 5,032,271
[45] Date of Patent: Jul. 16, 1991

[54] REVERSIBLE MECHANOCHEMICAL ENGINES COMPRISED OF BIOELASTOMERS CAPABLE OF MODULABLE INVERSE TEMPERATURE TRANSITIONS FOR THE INTERCONVERSION OF CHEMICAL AND MECHANICAL WORK

[75] Inventor: Dan W. Urry, Birmington, Ala.

[73] Assignee: Univeristy of Alabama at Birmingham/Research Foundation, Birmingham, Ala.

[21] Appl. No.: 410,018

[22] Filed: Sep. 20, 1989

Related U.S. Application Data

[63] Continuation of Ser. No. 163,388, Mar. 2, 1988, abandoned, which is a continuation-in-part of Ser. No. 900,895, Aug. 27, 1986, abandoned, and a continuation-in-part of Ser. No. 62,557, Jun. 15, 1987, abandoned.

[51] Int. Cl.$^5$ .............................................. B01D 33/00
[52] U.S. Cl. ..................................... 210/350; 210/356; 60/673
[58] Field of Search ......................... 210/350, 351, 356

[56] References Cited

U.S. PATENT DOCUMENTS

| | | |
|---|---|---|
| 3,180,825 | 4/1965 | Couvreur et al. |
| 3,669,879 | 6/1972 | Berriman |
| 3,821,108 | 6/1974 | Manjikian |
| 4,132,746 | 1/1979 | Urry ................................. 528/328 |
| 4,208,289 | 6/1980 | Bray |
| 4,500,700 | 2/1985 | Urry ................................. 528/328 |

Primary Examiner—Allen M. Ostrager
Attorney, Agent, or Firm—Richard L. Neeley

[57] ABSTRACT

A mechanochemical engine cpaable of desalinating sea water or brackish water by the conversion of mechanical work to chemical work, which comprises: a) a housing containing an elastomeric material capable of being stretched, to thereby allow salt-diminished water to move into the elastomeric material, while substantially repelling solvated salt ions from entry thereto, b) means for stretching and relaxing said elastomeric material in said housing, in connection with said elastomeric material; and c) means for uptake of said sea water or brackish water into said housing, means for draining concentrated salt water from said housing, and means for draining desalinated water from said housing.

18 Claims, 8 Drawing Sheets

REVERSIBLE MECHANOCHEMICAL ENGINES COMPRISED OF BIOELASTOMERS CAPABLE OF MODULABLE INVERSE TEMPERATURE TRANSITIONS FOR THE INTERCONVERSION OF CHEMICAL AND MECHANICAL WORK

BACKGROUND OF THE INVENTION

This application is a continuation of application Ser. No. 163,388, filed on Mar. 2, 1988, now abandoned, which is a continuation-in-part of U.S. Ser. No. 06/900,895 filed on Aug. 27, 1986 abandoned and U.S. Ser. No. 062,557 filed on June 15, 1987 abandoned.

FIELD OF THE INVENTION

The present invention relates to mechanochemical engines comprised of bioelastomers capable of modulable inverse temperature transitions for the interconversion of chemical and mechanical work.

DESCRIPTION OF THE BACKGROUND

Recently, the present inventor described the preparation of bioelastomers which exhibit elastomeric force development which can be varied either as a function of temperature or as a function of the hydrophobicity of the repeating units of the elastomeric polymer. By reversibly changing the hydrophobicity of the polymer repeating units using a reversible chemical process such as protonation/deprotonation, the temperature of the inverse temperature transition of the bioelastomers can be reversibly shifted, thereby, in effect, turning "on" and "off" elastomeric force.

For example, in pending application Ser. No. 07/062,557, incorporated herein in its entirety, it was disclosed that by changing the relative hydrophobicity of the elastin polypentapeptide (PPP) repeating unit —VPGVG—$_n$, using an occasional functional group, such as glutamic acid, the temperature of the inverse temperature transition can be lowered by protonation of a carboxylate side chain, for example, and can be raised by deprotonating the carboxylic acid group to form the anion. Of course, when modifying the hydrophobicity, it is necessary to do so in a way such that elasticity is retained. This may be accomplished, for example, by substitution at position 4 in the PPP repeating unit. With such a polymer, lowering the pH causes contraction and raising the pH causes relaxation.

Alternatively, the development of elastomeric force in different elastomers can be varied as a function of temperature by changing the hydrophobicity using Ile in place of Val, for example, at position 1. For example, in pending application Ser. No. 900,895, it was disclosed that cross-linked elastin polypentapeptide (PPP) and polytetrapeptide (PTP) and analogs thereof exhibit elastomeric force development at different temperatures spanning a range of up to about 75° C. depending upon several controllable variables. Ser. No. 900,895 is also incorporated herein in the entirety.

Using these elastomeric systems, the present inventor has described in Ser. No. 062,557 the construction of molecular machines utilizing entropic motive force in elastomeric protein systems. As a simple example, a weight may be suspended from a synthetic elastomeric PPP band at 20° C. in water. The band is formed on γ-irradiation of —Val$^1$-Pro$^2$-Gly$^3$-Val$^4$-Gly$^5$—$_n$, where n > 100 and the composition is approximately 40% peptide and 60% water by weight at 40° C. On raising the temperature from 20° C. to 40° C., the weight is raised against gravity to a fraction of the 20° C. length depending upon the load. Thus, for a band 10 cm in length, an appropriate weight would be raised 3 cm, for example, against the pull of gravity.

The immediately preceding example is one of converting thermal energy into mechanical work, i.e., thermomechanical transduction. However, it has now been found possible to design mechanochemical engines whereby mechanical work may be reversibly converted into chemical work, i.e., mechanochemical transduction. In accordance with the present invention, mechanochemical engines are provided using modulable inverse temperature transitions in the reversible interconversion of chemical and mechanical work.

For some years, it has been known that high salt concentrations can be used to lower the transition temperature for thermal denaturation of proteins. These salts are believed to interfere with electrostatic interactions in proteins, and also to increase the solubility of the peptide bond moiety in water. See Proteins: Structures and Molecular Properties (Freeman 1984). Using this principle, it has also been shown that a belt of collagen can be made to contract on introduction into a medium of high salt concentration. In 1965, for example, a mechanochemical engine was designed based upon the reversible contraction of partially cross-linked collagen by treating the collagen with a strong aqueous solution of lithium bromide, potassium thiocyanate or urea. By washing the fibers with water or dilute solution, the process was reversed, leading to elongation or relaxation of the collagen. However, as relatively high heats of denaturation are involved, large concentration gradients are required. In a description of such a mechanochemical engine in Katchalsky et al, *Nature*, pages 568–571 (May 7, 1966), two baths were used having a concentration of 11.25 M LiBr with a second bath having a concentration of no more than 0.3 M LiBr.

In such a mechanochemical engine the contraction-relaxation cycle can be repeated many times by bringing the collagen fiber sequentially into contact with one very dilute and then with a second very concentrated solution of LiBr. During this process, the solutions become mixed and the net mechanical work obtained in such a cyclical operation relates to the free energy of mixing of these solutions. In such an engine, it is the free-energy change due to the transfer of salt from the concentration solution to the dilute solution, and to the associated water flow, that is converted partly into mechanical work. However, a major disadvantage of the collagen-based engine is that the use of large concentration gradients and uncommon salts and denaturants is required. Indeed, it would be very advantageous if mechanochemical engines could be designed utilizing relatively small concentration gradients and common salts such as sodium chloride. This would utilize an operational principle other than the thermal denaturation of proteins.

SUMMARY OF THE INVENTION

Accordingly, it is an object of the present invention to provide a mechanochemical engine which relies upon a chemical potential driven contraction and relaxation of bioelastomers by ionic strength modulation of an inverse temperature transition, wherein relatively small salt concentration gradients may be used wherein, for example, sodium chloride may be used as an effective salt.

It is also an object of this invention to provide a mechanochemical engine for effecting desalination of sea water in a low energy intensive manner using the mechanical energy input of bioelastomer stretching in one design and stretching plus hydrostatic pressure in a second design.

It is also an object of the present invention to provide a process for effecting the desalination of sea water in a low energy intensive manner without relying upon conventional techniques such as distillation, ion exchange or reverse osmosis.

Furthermore, it is an object of this invention to provide a mechanochemical engine for the development of chemical gradients or achieving chemical separations such as proton or hydroxyl gradients, or for the preparation of the reduced species of a redox couple, or for the preparation of ATP using the phosphorylated/dephosphorylated couple.

DETAILED DESCRIPTION OF THE PREFERRED EMBODIMENTS

I. Introduction

The present invention pertains, in general, to the use of elastomeric matrices of sequential polypeptides in mechanochemical engines. The elastomeric matrices are capable of exhibiting a chemical potential driven contraction and relaxation. For example, the elastomeric matrices used in accordance with the present invention may be made of the elastin polypentapeptide $(L-Val^1-L.Pro^2-Gly^3-L.Val^4-Gly^5)_n$. This polypentapeptide can also be described as $(VPGVG)_n$ or even PPP. This polypentapeptide is soluble in water in all proportions below 25° C., but upon raising temperature to 37° C. a phase separation occurs resulting in an overlying equilibrium solution and a more dense viscoelastic phase called a coacervate. Using a suitable mold, the coacervate can be formed into a desired shape. Furthermore, when very high molecular weight polymers are desired, for example having a value of n in the range of 100 to 200, $\gamma$-irradiation or chemical means or photochemical means can be used to effect cross-linking of the coacervate and to form an elastomeric matrix of a desired shape. Notably, all available chemical and photochemical means may be used, some of which are enumerated in U.S. Pat. No. 4,132,746, which is incorporated herein in the entirety.

In general, elastomers may be mechanically characterized by the use of a stress/strain curve which is a plot of the force required to extend (stress) versus the extent of elongation (strain). The slope of the curve at a particular extension divided by the cross-sectional area provides an elastic modulus referred to as the Young's modulus. For example, at 37° C., the elastic modulus of X-PPP, where X-designates cross-linked, varies over a range of $10^5$ to $10^7$ dynes/cm$^2$, depending upon the $\gamma$-irradiation dose, with a 20 Mrad dose affording a value of $10^6$ dynes/cm$^2$. Elastomers may also be characterized by thermoelasticity studies.

Figure 1:
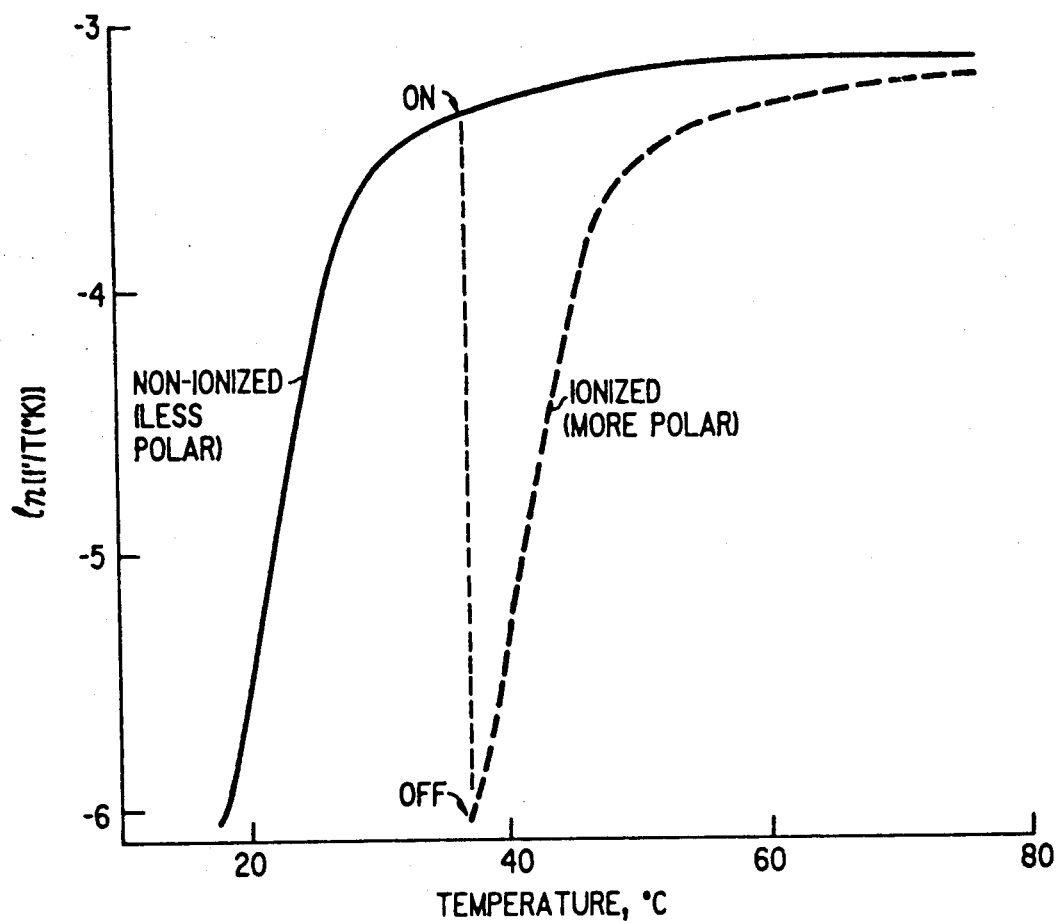

Notably, FIG. 1 illustrates a plot of data obtained when stretching a 20 Mrad cross-linked polypentapeptide, $X^{20}$-PPP, to a fixed extension, and monitoring the elastomeric force as a function of temperature. FIG. 1 shows a dramatic rise in elastomeric force occuring on going from 20° to 40° C., and above 40° C., the curve is essentially flat. The rapid rise in force is the result of an inverse temperature transition, the temperature of which is dependent on the hydrophobicity of a polypentapeptide, and the near zero slope above 40° C. reflects the dominantly entropic, or near ideal, nature of the elastomer. However, in addition to following force as a function of temperature at constant length, it is also possible to follow length as a function of temperature at constant force. When the latter is done, a dramatic contraction occurs for the present bioelastomers between 20° C. and 40° C. For example, on attaching a fixed weight, upon raising the temperature a few degrees, a weight can be lifted through a substantial distance, and thereby, mechanical work is performed. This is thermomechanical transduction. When carried out at constant length, the extension can be set in such a way that a dramatic rise in force can occur with but a small change in temperature.

Figure 2:
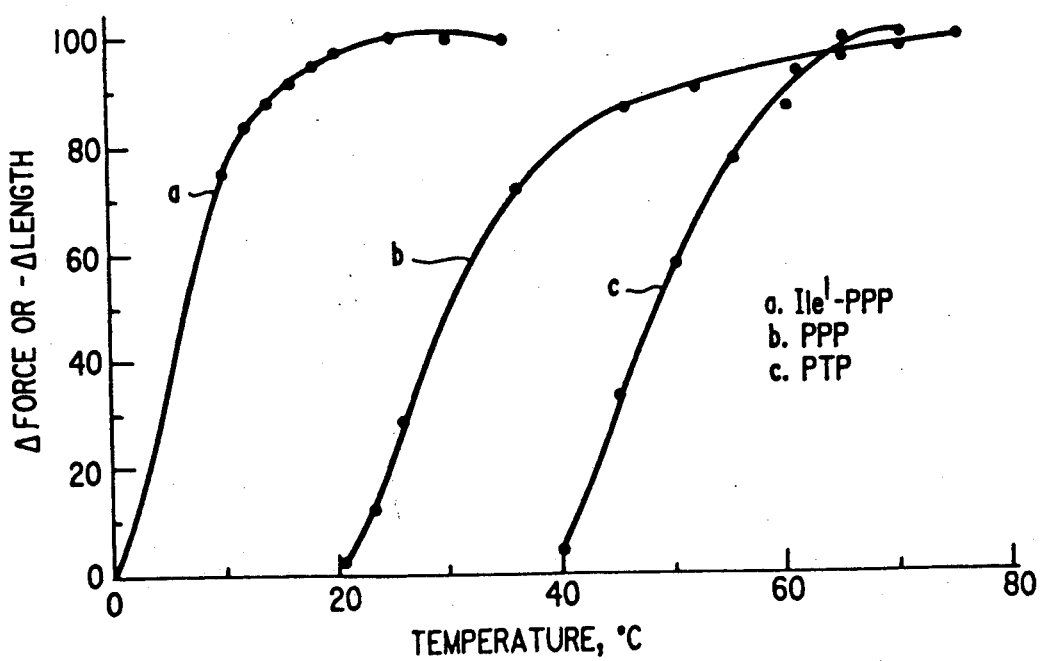

The dramatic contraction at fixed force or steep force development at fixed length occurs as the result of an inverse temperature transition and the temperature range over which such a transition occurs is inversely dependent on the hydrophobicity of the peptide chain. This was demonstrated in co-pending application Ser. No. 900,895. Accordingly, when the sequential polypeptides is made more hydrophobic, as in the sequence $(L.Ile^1-L.Pro^2-Gly^3-L.Val^4-Gly^5)_n$ which when cross-linked at 20 Mrad is designated as $X^{20}$-Ile$^1$-PPP, the contraction or development of elastomeric force occurs between 0° and 20° C. Alternatively, if a higher temperature for inverse temperature transition is desired, the sequential polypeptide may be made less hydrophobic to effect such a change. For example, when the sequential polypeptide is made less hydrophobic, as in the sequence $(L.Val^1-L.Pro^2-Gly^3-Gly^4)_n$, which when cross-linked can be designated as $X^{20}$-desVal$^4$-PPP or simply $X^{20}$-PPP, the contraction or development of elastomeric force occurs between 40° and 60° C. This is illustrated in FIG. 2. Thus, by changing the hydrophobicity, the thermally induced contraction can be made to occur over any desired temperature range from below 0° to about 75° C. Moreover, the development of near maximum elastomeric force occurs for these bioelastomers over a very narrow temperature range.

The process of inverse temperature transition is a function of the hydrophobicity of peptide side chains as described above. For example, when there are hydrophobic side chains of polypeptides exposed to water such as the side chains of the Ile, Val and Pro residues, water surrounding the hydrophobic side chains is more ordered than bulk water and is called clathrate-like water. On raising the temperature through the temperature of the inverse temperature transition, the clathrate-like water becomes less ordered bulk water as the hydrophobic side chains interact intermolecularly in the formation of a more ordered polypeptide.

Using the concept of an inverse temperature transition as described above, it has been found possible to effect either a polymer-based chemical modulation of an inverse temperature transition or a solvent-based chemical modulation of an inverse temperature transition. Both of these approaches can be used in designing mechanochemical engines in accordance with the present invention.

As noted above, by changing the hydrophobicity of the sequential polypeptide, the temperature range over which the inverse temperature transition occurs can be shifted. Thereby, polypeptides can be designed in which hydrophobicity can be changed by a reversible chemical process such as protonation and deprotonation. In the more polar, or less hydrophobic, state, involving the carboxylate anion (COO−), for example, the inverse temperature transition occurs over a higher temperature range as in the dashed curve of FIG. 1. In the less polar, or more hydrophobic, state, on shifting to a protonated carboxyl group (COOH), for example, the inverse temperature transition occurs over a lower temperature range as in the solid curve of FIG. 1. Thus, it is now possible at a fixed temperature, to have the elastomer relaxed at high pH where the COO− species, for example, is dominant, and to then cause the elastomer to contract by lowering the pH to where the COOH species is the dominant species. This is chemomechanical transduction.

In order to illustrate this aspect of the present invention, an example will now be provided for the purpose of illustration only and which is not intended to limit the present invention. In the example, as elsewhere in this application, standard one-letter and three-letter abbreviations are used for amino acids.

EXAMPLE

Figure 3:
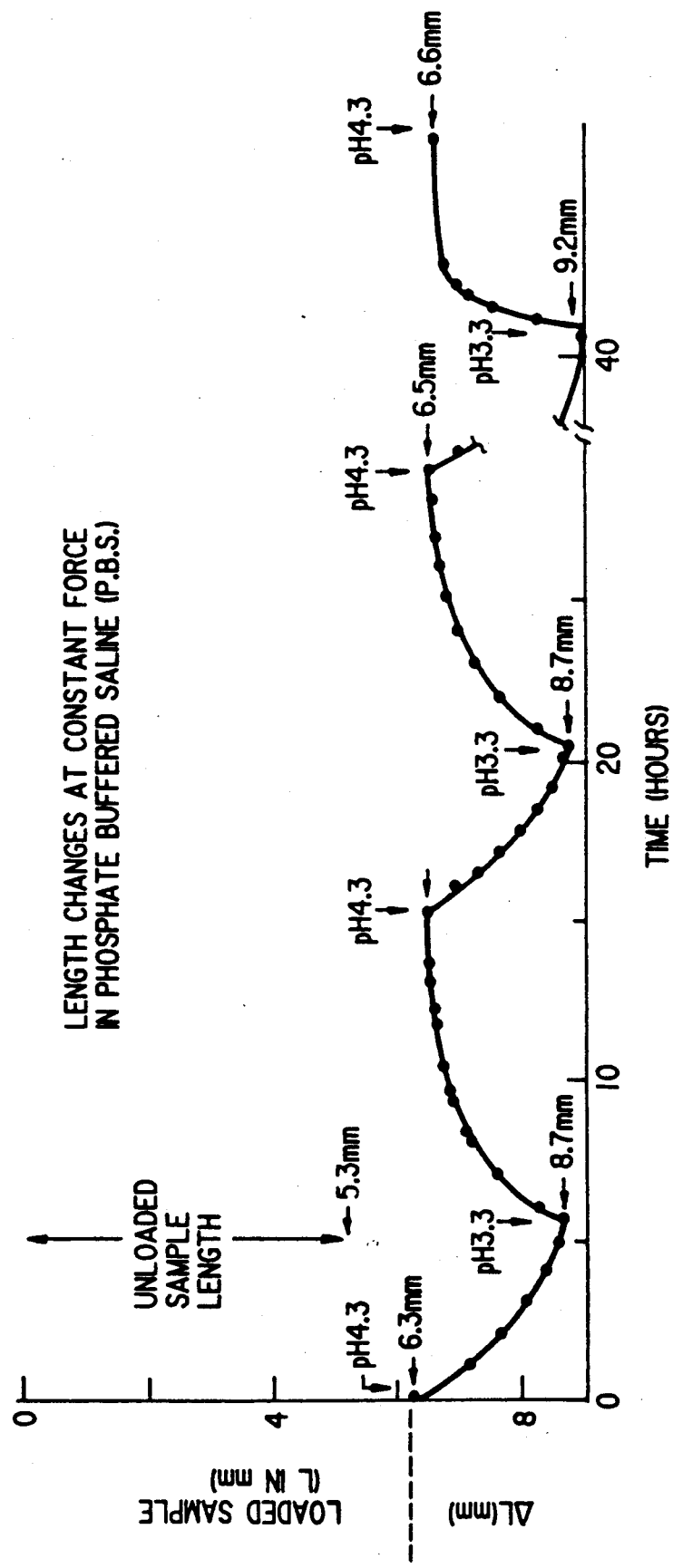
Figure 4:
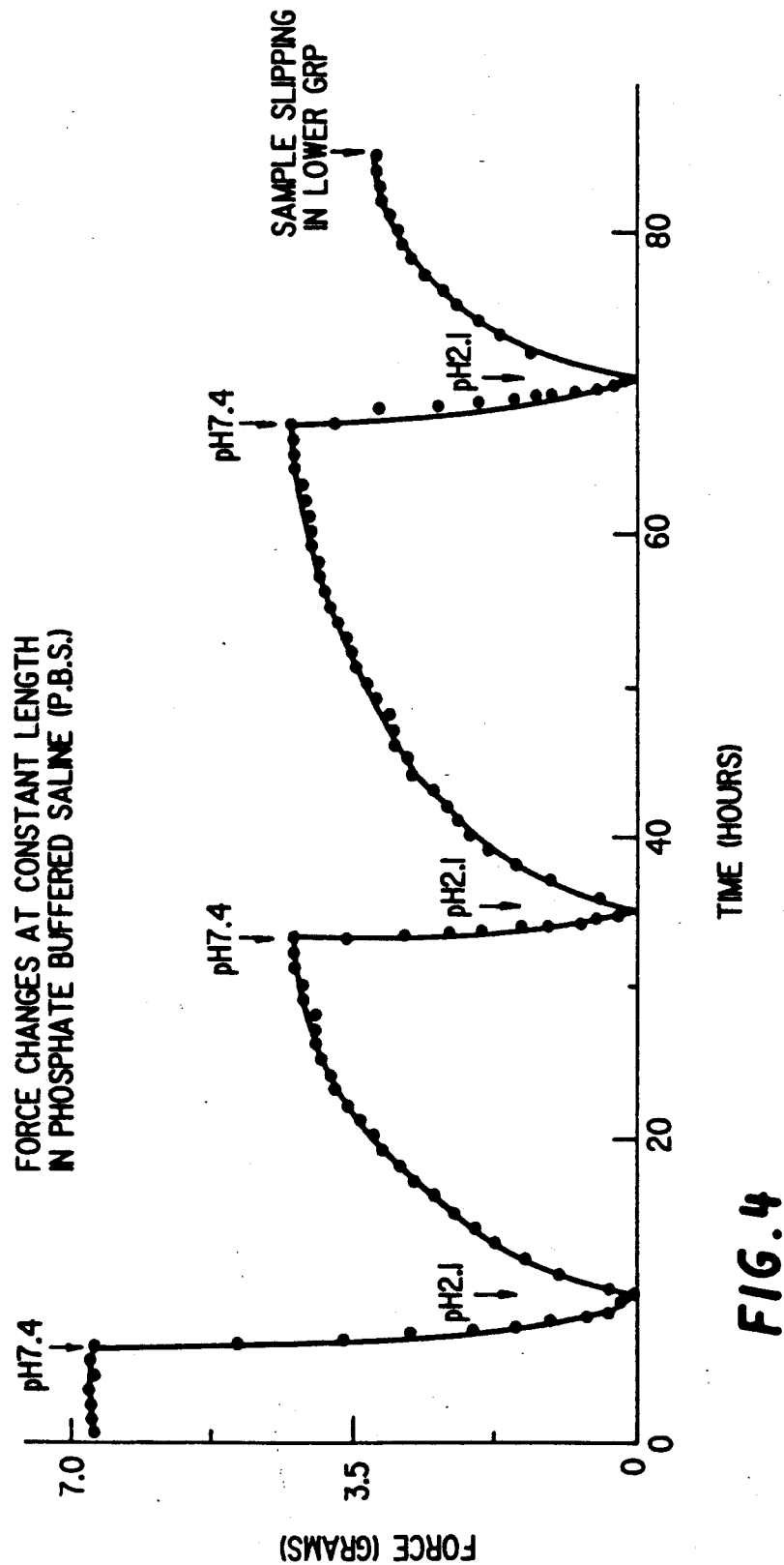

A polypeptide was synthesized having the formula poly[(VPGVG), (VPGEG); 4:1] where E is the glutamic acid residue, Glu. The polypeptide synthesized contained 4 Glu residues per 100 residues of polypeptide, thereby being designated as 4%-Glu-PPP. In phosphate buffered saline (PBS), which is 0.15 N NaCl and 0.01 M phosphate, this polypentapeptide coacervates in a similar temperature range to PPP in water when the pH is 3.0. Upon raising the pH to 7.0, the temperature of the transition systematically rises to 70° C. with a pK of about 4.5. On cross-linking, an elastomeric band of $X^{20}$-4%-Glu-PPP is obtained. This biomaterial is contracted at pH 3.0 and is relaxed at pH 7.0. At constant force, this biomaterial is seen in FIG. 3 to contract lifting the weight at pH 3.3 and to relax lowering the weight at pH 4.3. At constant length, using an unnecessarily wide pH range in FIG. 4, the biomaterial develops force as shown at pH 2.1 and turns off force at pH 7.4. It can thereby repeatedly raise and lower a weight 1000 times its own dry weight.

Figure 5:
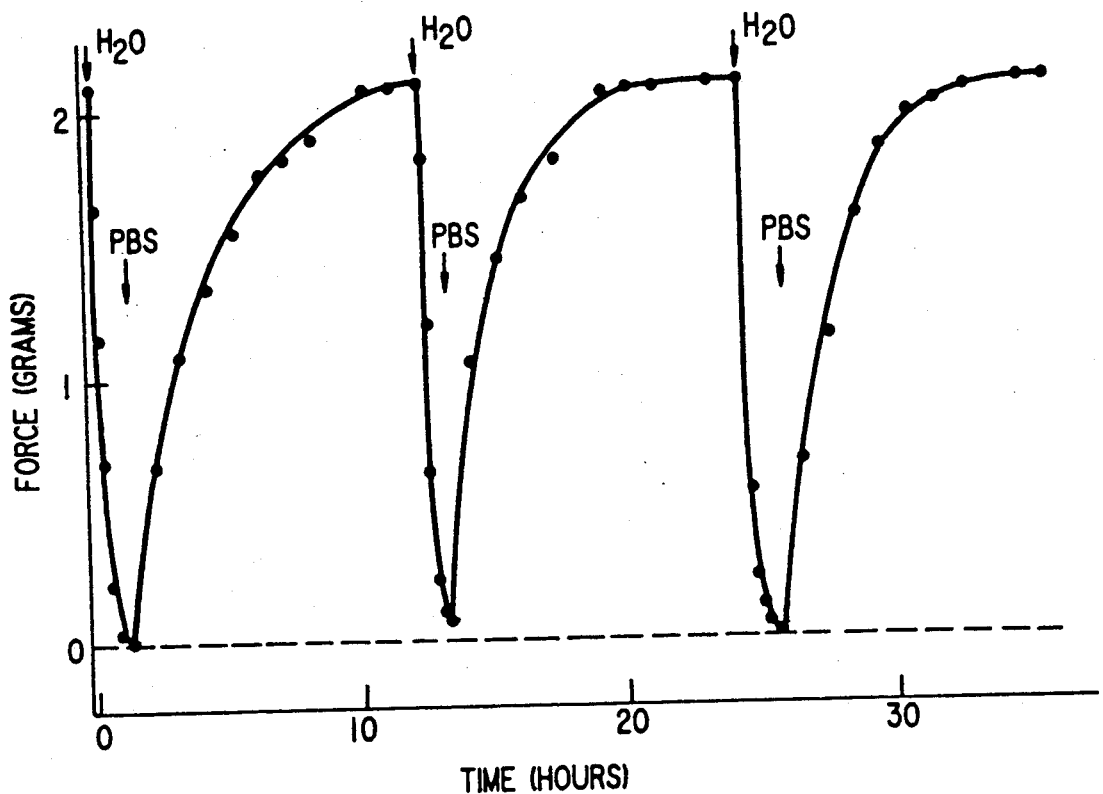
Figure 6:
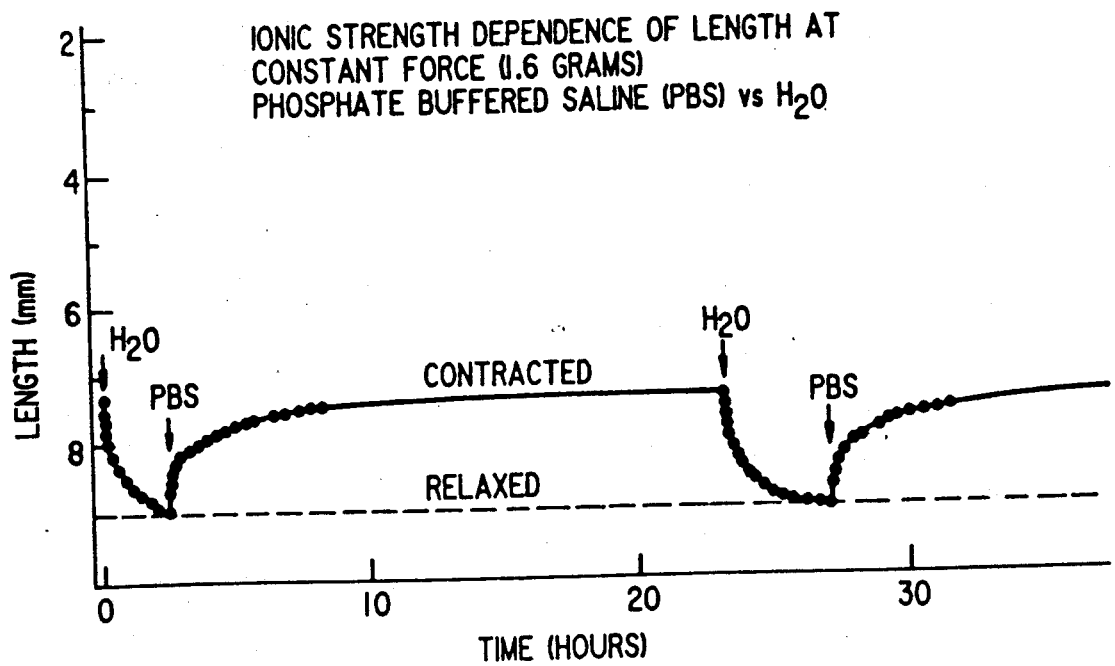

However, in addition to the above mechanism of chemomechanical transduction, the present bioelastomers are susceptible to a solvent-based mechanism whereby the temperature of an inverse temperature transition may be shifted. In this mechanism, the clathrate-like water surrounding the hydrophobic side chains is destabilized by changes in the chemical potential of the solvent or medium, without any change in the chemical nature of the polypeptide to lower the temperature of the inverse temperature transition. For example, this may be accomplished simply by raising the salt concentration in the medium. In this mechanism, ions are postulated to draw water molecules into their solvation shells, thereby shifting the equilibrium of the possible water structures away from that of the clathrate-like structure. Such a mechanism can be used, perhaps, to explain the lowering of the temperature for coacervation of PPP upon increasing the salt concentration as well as lowering the temperature of the inverse temperature transition of $X^{20}$-PPP. In this mechanism, there is essentially no effect of change in pH. Thus, at the appropriate temperature, which is 25° C. for $X^{20}$-PPP, it is possible at constant load force to have $X^{20}$-PPP largely relaxed at 25° C., and, on changing to phosphate buffered saline (PBS) to bring about a contraction. This is shown in FIG. 5. Alternatively at constant length, raising the salt concentration causes the development of elastomeric force. This process is illustrated in FIG. 6.

As noted above, the present invention provides mechanochemical engines predicated upon the use of the above principles. In particular, a mechanochemical engine for effecting the desalination of sea water or brackish water is provided. In accordance with a very advantageous aspect of the present invention, a low energy intensive process for effecting desalination of sea water or brackish water is also provided. In accordance with the present invention, when, for example, $X^{20}$-PPP is stretched, hydrophobic groups become exposed; the elastomer takes up water in an exothermic reaction as the exposed hydrophobic groups become surrounded with clathrate-like water. This is similar to the swelling that occurs on lowering the temperature from 40° to 20° C., where there is a 10 fold increase in volume for $X^{20}$-PPP. The more hydrophobicity expressed by a polypeptide, the less favorable is the situation for ions. This is well demonstrated by the raised $pK_a$ of the Glu side chain for the more hydrophobic $X^{20}$-4%-Glu-Ile$^1$-PPP and by the raised $pK_a$ on stretching $X^{20}$-4%-Glu-PPP. In both cases, the increased expression of hydrophobicity results in the free energy for formation of the carboxylate anion being less favorable. Therefore, stretching $X^{20}$-PPP in a high salt solution results in the uptake of solution into the elastomer which is low in ions. The excess solution which is drained off while $X^{20}$-PPP is stretched, is at a higher salt concentration. When the fiber is relaxed it exudes a solution which is at a lower salt concentration. By appropriately repeating this process with directed solution flows, the result is the progressive splitting of a salt solution into two solutions one higher and the other lower in salt concentration. The use of this principle is schematically shown in FIG. 7, with a simple mechanical desalination device in accordance with the present invention.

In accordance with one aspect of the present invention, a mechanochemical engine may be constructed using the basic designs described hereinbelow and shown in FIG. 8a, b and c which are based upon Katchalsky. The engine is particularly characterized by the use of belts which are made of the elastomeric polypeptides of the present invention instead of collagen or rubber. Furthermore, the mechanochemical engines of the present invention are not driven merely by contractions and relaxations for reversible thermal denaturations or by means of charge-charge repulsion wherein $$(\partial \mu_i/\partial f)_{n_i} > 0$$

but rather by utilizing any reversible chemical process that would make the chemical moieties attached to the polypeptide chain either more or less polar, wherein $(\partial \mu_i/\partial f)_{n_i} < 0$, or a medium in which the polypeptide chain is placed that contains more or less salt. The case wherein $(\partial \mu_i/\partial f)_{n_i} < 0$ arises from a stretch-induced increase in $pK_a$ when the charged species is an anion, for example.

Figure 7:
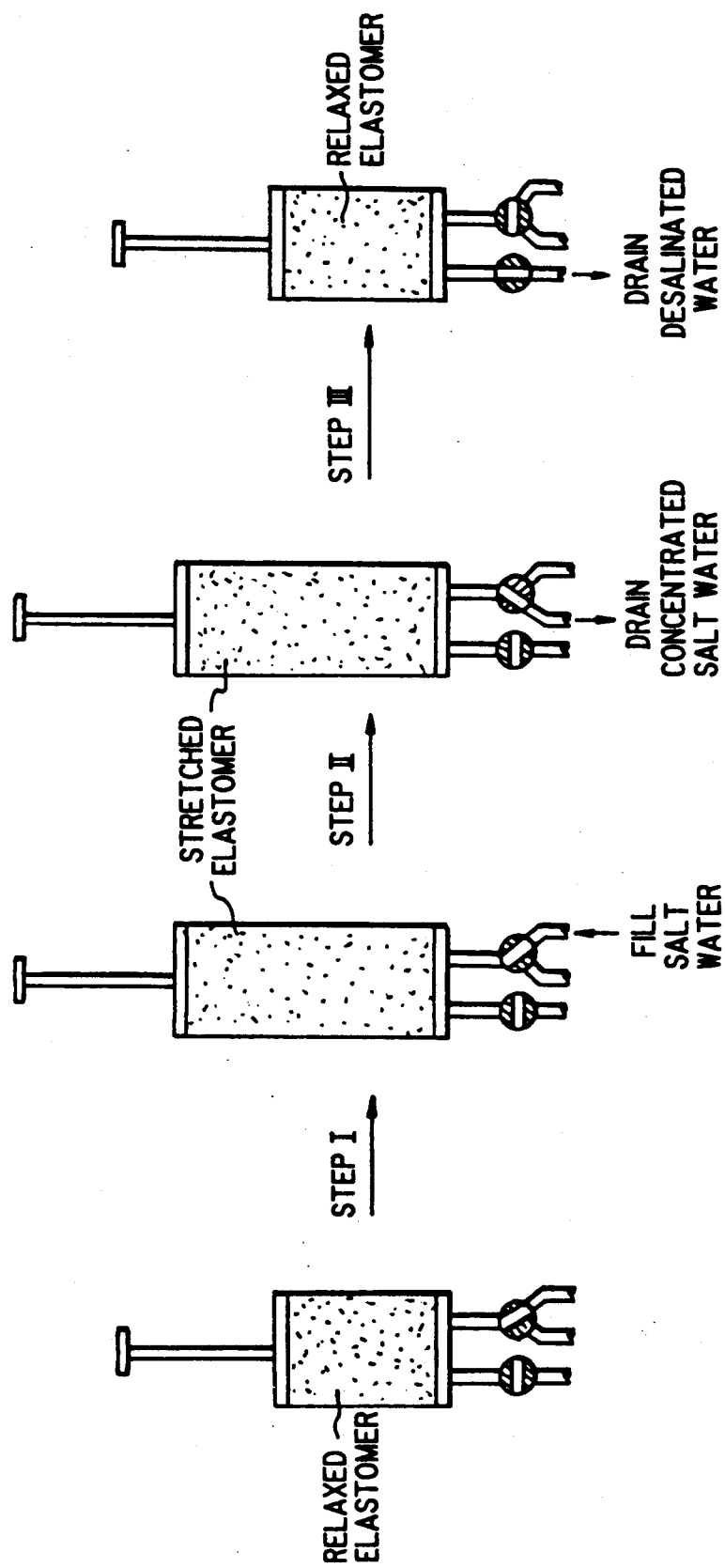

In accordance with the present invention, the elastomeric materials disclosed herein may be used to design a variety of mechanochemical engines with the basic configuration shown in FIG. 7 being, perhaps, the simplest embodiment.

The elastomeric materials may be used, as noted above for desalination using a solvent-based mechanism to convert mechanical work into chemical work. This may also entail a polymer-based mechanism. In polymer-based systems, several variations may be noted, all having to do with the development of chemical gradients.

First, a mechanochemical engine may be designed to prepare [H+] or [OH−] containing solutions. Secondly, the engine may also be used to prepare a reduced component of a redox couple. Thirdly, for example, the engine may be used to prepare ATP from ADP and phosphate. Other uses may be envisioned.

Alternatively, a solvent-based mechanism may be used in the operation of an engine converting mechanical work to chemical work. An example of this is a desalination apparatus disclosed herein.

Finally, a solvent-based mechanism may also be used in the operation of an engine which converts chemical work to mechanical work. An example of this is a mechanochemical engine disclosed herein which utilizes the present elastomeric materials instead of the collagen or rubber used in the previously described Katchalsky engine.

II. The Elastomeric Materials

Elastin is comprised of a single protein. The sequence of elastin can be described as a serial alignment of alanine-rich, lysine-containing cross-linking sequences alternating with glycine-rich hydrophobic sequences. With the entire bovine sequence known, the most striking hydrophobic sequences, both from the standpoint of length and of composition, are one that contains a polypentapeptide (PPP) and one that contains a polyhexapeptide (PHP). Elastin also contains a repeating polytetrapeptide (PTP). As a result of earlier work conducted by the present inventor, the polypentapeptide of elastin when cross-linked has been found to be elastomeric and the polyhexapeptide thereof has been found to be non-elastomeric and appears to provide a means for aligning and interlocking the chains during elastogenesis. From the present work, it has now also been found that the elastin polypentapeptide and polytetrapeptide are both conformation-based elastomers that develop entropic elasticity on undergoing an inverse temperature transition to form a regular $\beta$-turn containing dynamic structure.

A typical biological elastic fiber is comprised of a large elastin core covered with a fine surface layer of microfibrillar protein. Elastin is formed upon cross-linking of the lysine residues of tropoelastin. The repeating elastin pentapeptide has the formula $(VPGVG)_n$, while the repeating hexapeptide has the formula $(VAPGVG)_n$, where n varies depending upon the species. The repeating polytetrapeptide unit has the formula $(VPGG)_n$. These sequences, of course, utilize the standard one-letter abbreviation for the constituent amino acids.

It has been found that these polypeptides are soluble in water below 25° C., but on raising the temperature they associate in the polypentapeptide (PPP) and polytetrapeptide (PTP) cases, reversibly to form a viscoelastic phase, and in the polyhexapeptide (PHP) case, irreversibly to form a precipitate. On cross-linking, the former (PPP) and (PTP) have been found to be elastomers.

In part, the present invention resides in the discovery that at temperatures above 25° C. in water, PTP and PPP exhibit aggregation and form a water-containing viscoelastic phase, which upon cross-linking by $\gamma$-irradiation forms an elastomer. By contrast, PHP forms a granular precipitate, which is not elastomeric. In fact, it has been found that for potential elastomers, such aggregation is readily reversible, whereas for non-elastomeric samples, such as PHP, temperature-driven aggregation is irreversible and redissolution usually requires the addition of trifluoroethanol to the aggregate.

For purposes of clarification, it is noted that the reversible temperature elicited aggregation, which gives rise upon standing to a dense viscoelastic phase, is called coacervation. The viscoelastic phase is called the coacervate, and the solution above the coacervate is referred to as the equilibrium solution.

Most importantly, however, cross-linked PPP, PTP and analogs thereof exhibit elastomeric force development at different temperatures spanning a range of up to about 75° C. depending upon several controllable variables. Moreover, these cross-linked elastomers develop near maximum elastomeric force over a very narrow temperature range. Thus, by synthesizing bioelastomeric materials having varying molar amounts of the constituent pentamers and tetramers together with such units modified by hexameric repeating units, and by choosing a particular solvent to support the initial viscoelastic phase, it is possible to rigorously control the temperature at which the obtained bioelastomer develops elastomeric force.

In general, the process of raising the temperature to form the above elastomeric state is an inverse temperature transition resulting in the development of a regular non-random structure, unlike typical rubbers, which utilizes, as a characteristic component, hydrophobic intramolecular interactions. The regular structure is proposed to be a $\beta$-spiral, a loose water-containing helical structure with $\beta$-turns as spacers between turns of the helix which provides hydrophobic contacts between helical turns and has suspended peptide segments. These peptide segments are free to undergo large amplitude, low frequency rocking motions called librations. Consequently, a new mechanism of elasticity has now been developed called the librational entropy mechanism of elasticity.

The elastomeric force of these various bioelastomers develops as the regular structure thereof develops. Further, a loss of regular structure by high temperature denaturation, results in loss of elastomeric force. Interestingly, this situation is just the reverse of that for the random-chain-network theory of elasticity, in which the more nearly random the polypentapeptide, the less the elastomeric force, and the more developed the $\beta$-turn containing structure, the greater the elastomeric force.

In the broadest sense, a new entropy-based mechanism of elasticity is presented for use herein. The mechanism therefor appears to be derived from a new class of polypeptide conformations called $\beta$-spirals wherein $\beta$-turns recur with regularity in a loose water-containing helix. The $\beta$-spiral is the result of intramolecular interturn hydrophobic interactions which form on raising the temperature in water. In the $\beta$-spiral of the elastomeric polypentapeptide of elastin, $(Val^1-Pro^2-Gly^3-Val^4-Gly^5)_n$, the type II $Pro^2-Gly^3$ $\beta$-turns function as spacers, with hydrophobic contacts, between the turns of the helix, which results in the segments of $Val^4-Gly^5-Val^1$ being suspended. Being essentially surrounded by water, the peptide moieties of the suspended segments are free to undergo large rocking motions referred to as librations which become damped on stretching. The decrease in amplitude of librations on stretching constitutes a decrease in entropoy and it appears that the decrease in free energy due to the increase in entropy on returning to the relaxed state is the driving force for elastomeric retraction.

Upon raising the temperature of the polypeptide-solvent system, such as PPP-water, for example, the hydrophobic side chains such as those of Pro and Val when dispersed in water are surrounded by water having a clathrate-like structure, that is, by water that is more ordered than normal bulk water. Upon raising the temperature, an amount of this more ordered clathrate-like water surrounding the hydrophobic groups becomes less ordered bulk water as the hydrophobic chains associate to form a more ordered polypeptide. It appears that it is the optimization of intramolecular hydrophobic contacts that assists the polypeptide in wrapping up into a loose helix. Adherence to the Second Law of Thermodynamics appears to be maintained by the requirement that the decrease in entropy of the polypeptide portion of the system be less than the increase in entropy of the water in system. Since $\Delta G = 0$ at the temperature midpoint ($T_{mp}$) of a structural transition between a pair of states, then $T_{mp} = \Delta H / \Delta S$. If the entropy change, $\Delta S$, derives from the hydrophobicity of the repeating unit, as it would in the clathrate-like water mechanism, than an increase in the hydrophobicity of the repeating unit can be used to explain the decrease in $T_{mp}$, the midpoint of the inverse temperature transition. In fact, a decrease in the hydrophobicity of the repeating unit results in an increase $T_{mp}$. Conversely, an increase in the hydrophobicity of the repeating units results in a decrease in $T_{mp}$.

The above principle is demonstrated by substituting the more hydrophobic isoleucine (Ile) for valine (Val) in the elastin polypentapeptide, $(Ile^1-Pro^2-Gly^3-Val^4-Gly^5)_n$, i.e., $Ile^1$-PPP, to produce a substituted polypentapeptide which has properties similar to PPP, except that the described transition occurs at a lower temperature.

For purposes of clarity, it is noted that for the above numbered sequence and all sequences hereafter, the superscript numbering system is a sequence numbering based upon the dominant secondary structural feature of these repeating sequences which is the type II $Pro^2$-$Gly^3$ $\beta$-turn, a ten atom hydrogen bonded ring involving the $C=O$ of residue 1 and the NH of residue 4.

The present elastomeric materials also extend to the polytetrapeptide of elastin. It is recalled that this repeating unit has the formula $(Val^1-Pro^2-Gly^3-Gly^4)_n$, which also forms a $\beta$-spiral similar to PPP. However, the temperature of aggregation for PTP occurs at a higher temperature than for PPP. In essence, for both the polypentapeptide and polytetrapeptide repeating units of elastin, it has been found that the temperature of the transition for the development of elastomeric force is proportional to the hydrophobicity of the repeating unit. Hence, two important principles have been elucidated. First, elastomeric force development occurs due to an inverse temperature transition resulting in increased polypeptide order by raising the temperature. Secondly, the temperature of this transition for the development of elastomeric force is proportional to the hydrophobicity of the repeating unit in the bioelastomer.

Analogs of both the elastin polypentapeptide PPP and the polytetrapeptide (PTP) and combinations thereof are contemplated for use in the present invention. For example, it has been found that the temperature of transition for $Ile^1$-PPP shifts to a lower temperature by an amount calculable from the increase in hydrophobicity relative to PPP using hydrophobicity. Thus, by carefully choosing a new analog with a different repeating unit hydrophobicity, the transition temperature for the development of elastomeric force can be predictably shifted to a different temperature. In fact, by judiciously selecting various repeating units and combinations thereof, along with various solvent mixtures it is now possible to select a transition temperature from within a range of up to about 75° C., from about $-25°$ C. to about $+50°$ C.

Additionally, the elastin polyhexapeptide (PHP) may also be incorporated in various amounts in the elastomeric materials of the present invention as will be discussed below.

As stated above, the most striking repeating sequence of elastin polypentapeptide is the polypentapeptide $(Val^1-Pro^2-Gly^3-Val^4-Gly^5)_n$, wherein, for example, n is 11 for cows and pigs. The polypentapeptide is soluble in water at all proportions below 25° C. On raising the temperature above 25° C., aggregation occurs and the aggregate settles to form a dense viscoelastic phase, called the coacervate that at 40° C. is about 38% peptide and 62% water by weight. The process of PPP coacervation, as noted, is entirely reversible. Moreover, on crosslinking, the PPP coacervate is found to be elastomeric. The coacervate concentration of PPP as well as the elastomeric $\gamma$-irradiation cross-linked PPP coacervate undergo an inverse temperature transition, which commences at 25° C. and which reaches completion near 37° C. Over the same temperature range in a thermoelasticity study starting at 60% extension and 40° C., the elastomeric force of the cross-linked PPP coacervate increases dramatically from near zero at 20° C. to full force near 40° C. Above 40° C., the elastomeric force divided by the temperature (°K.) becomes quite constant.

This indicates that the cross-linked PPP is a dominantly entropic elastomer. That is, the entropic component of the elastomeric force depends upon the decrease in numbers of low energy states accessible to the polymer on extension, whereas the internal energy component of elastomeric force results from stressing of bonds which would increase the probability of rupture of the elastomer.

Thus, in part, the present invention is predicated upon the earlier finding that it is possible to change the temperature of transition by modifying the PPP. In particular, it has been found that by increasing the hydrophobicity of the PPP repeating unit, the viscoelastic phase transition occurs at lower temperatures, while by decreasing the hydrophobicity of the repeating units, this transition occurs at higher temperatures. Of course, when modifying the hydrophobicity, it is necessary to do so in a way such that elasticity is retained.

For example, modifications of the repeating pentamers have been made which destroy the molecular structure required for elasticity, such as the $Ala^1$ and $Ala^5$ analogs. The $Ala^1$ and $Ala^5$ analogs, the former decreasing and the latter increasing pentamer hydrophobicity, result in the formation of granular precipitates on raising the temperature of aqueous solutions rather than forming viscoelastic coacervates and $\gamma$-irradiation cross-linking of the $Ala^5$-PPP precipitate results in a hard material that simply breaks upon stretching. In accordance with the present discovery, it is believed that these analogs fail to produce elastomeric polymers for different but consistent reasons. First, the Ala¹ analog does not appear to allow for important Val¹ γYCH₃ ... Pro²δCH₂ intramolecular hydrophobic contacts required to form a viscoelastic coacervate. The Ala⁵ analog appears to interfere with librational motions in the Val⁴-Gly⁵-Val¹ suspended segment of the proposed PPP molecular structure. As noted, the librations are central to the proposed librational entropy mechanism of elasticity.

By contrast, the hydrophobicity of the repeating pentamer can be easily increased by introducing a-CH₂- moiety, for example, in residue 1 while maintaining β-branching, that is, to utilize the Ile¹ analog of PPP, i.e., (Ile¹-Pro²-Gly³-Val⁴-GLy⁵)$_n$. With a greater than 50,000 molecular weight, Ile¹-PPP reversibly forms a viscoelastic coacervate with the onset of coacervation being at 8° C. rather than 24° C. as for unsubstituted PPP. It appears from circular dichroism data that Ile¹-PPP and PPP have identical conformations both before and after the transitions and that the transition to increased intramolecular order on increasing the temperature is also shifted by 15° C. or more to lower temperatures. Further, the dramatic increase in elastomeric force on raising the temperature of the γ-irradiation cross-linked coacervate is similarly shifted to a lower temperature for the Ile¹-PPP analog. Thus, with this analog, a coupling of temperature dependent elastomeric force development and molecular structure is demonstrated. This, of course, means that it is now possible to rationally design polypeptide elastomers that undergo transitions at different temperatures and that would function as entropic elastomers in different temperature ranges.

As noted above, by increasing the hydrophobicity of PPP, such as by substituting Ile¹ for Val¹ in the pentameric sequence of -(VPGVG)$_n$ to form -(IPGVG)$_n$, it is now possible to accomplish at least two distinct objectives.

First, it is now possible to prepare, for example, the "homopolymeric" polypentapeptide of -(IPGVG)$_n$, i.e., Ile¹-PPP, which, as noted dissolves in water at 4° C., and upon raising the temperature to 8° C., exhibits aggregation. After cross-linking the coacervate by γ-irradiation, it is observed that essentially full elastomeric force is exhibited at about 25° C. for the cross-linked Ile¹-PPP as opposed to the 40° C. temperature required for the unsubstituted PPP. Thus, the temperature ordered transition for Ile¹-PPP occurs at a temperature approximately 15° C. lower than for PPP.

Secondly, it is now also possible to prepare mixed "copolymers", for example, of the polypentapeptides -X¹-(IPGVG)$_n$-Y¹- and -X²-(VPGVG-)$_n$-Y²- which exhibit variable and controllable transition temperatures which are in between the separate transition temperatures of PPP and Ile¹-PPP. Further, a great degree of control is possible inasmuch as the transition temperature obtained is directly proportional to the molar ratios of the respective pentapeptides incorporated therein.

Perhaps the most striking feature of the increased hydrophobicity PPP cross-linked analogs is that nearly full elastomeric force can be reached over a very narrow temperature range. For example, for cross-linked Ile¹-PPP, it is found that the elastomeric force thereof shows an abrupt increase from essentially zero at 8° C. to three-quarters of full force at 10° C., and essentially full force by 20°-25° C. Such an increase in elastomeric force over only a 2° C. temperature differential is, indeed, unprecedented and can be controlled by the percent extension in relation to swelling of the elastomer on lowering the temperature.

Although Ile¹-PPP is an excellent example of an increased hydrophobicity PPP analog, any PPP analog, which reduces the hydrophobicity of the repeating pentameric unit, while retaining the elasticity of the polypeptide, and without interfering with either the formation of the viscoelastic coacervate or the librational motion is within the ambit of the present invention.

For example, in addition to repeating unit sequences of —IPGVG—$_n$, using Ile¹, it is also possible to effect a variety of other substitutions. In general, a pentapeptide repeating unit of the formula:

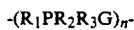

$-(R_1PR_2R_3G)_n-$ is within the ambit of the present invention, wherein R₁ is selected from the group consisting of Phe, Leu, Ile, and Val; R₂ is selected from the group consisting of Ala and Gly; R₃ is selected from the group consisting of Phe, Leu, Ile, and Val; and n is an integer from 1 to 200; and P is L-proline and G is glycine.

Notably, the above substitutions modify the hydrophobicity of the repeating unit so as to attenuate the transition temperature for near maximum elastomeric force development, of course, without destroying the elasticity of the bioelastomer.

In the above formula, it is noted that the amino acid Leu is, of course, Leucine. R₁, R₂ and R₃ correspond to positions 1, 3 and 4 in the numbered sequence as described herein.

Using Phe¹-PPP in water, it is possible to shift the temperature of transition initiation from 25° C. for PPP to about 0° C. Furthermore, this shift can be driven to even lower temperatures by utilizing mixed solvent systems of water/ethylene glycol or water/dimethyl sulfoxide (DMSO). For example, by using the Phe¹-PPP/water-ethylene glycol system, a transition temperature of as low as about −25° C. can be obtained. of course, a range of transition temperatures can be obtained between 0° C. and about −25° C. for the Phe¹-PPP/water-ethylene upon glycol system depending upon the amount of ethylene glycol added. It has been found that very low transition temperatures are obtained using approximately 50/50 mixtures of water-/ethylene glycol.

Conversely, the maximum shift to higher transition temperatures is limited by the denaturation of the polypeptide. With the present elastomeric polypeptides, this upper limit appears to be about 50° C., with denaturation beginning above 60° C.

However, as noted previously, the present invention includes not only PPP analogs, such as Ile¹-PPP, Phe¹-PPP or Ala³-PPP but all PPP analogs, and bioelastomers containing the same, which have transition temperatures, and, hence, temperatures of near maximum elastomeric force development, which are different from PPP; while retaining elasticity. Given, the present disclosure, one skilled in the art could clearly ascertain additional PPP analogs, and bioelastomers incorporating the same which meet the above criteria.

As noted above, the increased hydrophobicity analog, such as Ile¹-PPP may be synthesized as a "homopolymer", or a "copolymer" of -X²-(VPGVG-)$_n$-Y²- and -X¹-(IPGVG-)$_n$-Y¹- may be synthesized with the molar ratio of the constituent pentamers being dependent upon the desired temperature for elastomeric force development. However, in general, in such "copolymers", the -X$^1$-(IPGVG-)$_n$-Y$^1$-pentameric component is present in about 1-99% of the total pentameric molar content, while the -X$^2$-(VPGVG-)$_n$-Y$^2$-pentameric component is present in about 99-1% of the total pentameric molar content. More preferably, the -X$^1$-(IPGVG)$_n$-Y$^1$- component is present in about 5-95% of the total pentameric molar content, while the -X$^2$-(VPGVG-)$_n$-Y$^2$- component is present in about 95-5% of the total pentameric molar content. However, any combination of relative molar amounts can be used as dictated by the desired transition temperature.

Thus, in accordance with one aspect of the present invention, bioelastomers can be prepared which contain elastomeric units comprising tetrapeptide, or pentapeptide or units thereof modified by hexapeptide repeating units and mixtures thereof, wherein said repeating units comprise amino acid residues selected from the group consisting of hydrophobic amino acid and glycine residues, wherein the repeating units exist in a conformation having a β-turn which comprises a polypentapeptide unit of the formula:

wherein I is a peptide-forming residue of L-isoleucine;
P is a peptide-forming residue of L-proline;
G is a peptide-forming residue of glycine;
V is a peptide-forming residue of L-valine;
and wherein X is PGVG, GVG, VG, G or a covalent bond; Y is IPGV, IPG, IP or I or a covalent bond; and n in both formulas is an integer from 1 to 200; or n is 0, with the proviso that X$^1$ and Y$^1$ together constitute a repeating pentapeptide unit, in an amount sufficient to adjust the development of elastomeric force of the bioelastomer to a predetermined temperature.

However, the present invention also relates, as noted above, to the earlier discovery of bioelastomers which contain elastomeric units comprising tetrapeptide, or pentapeptide or units thereof modified by hexapeptide repeating units and mixtures thereof, wherein said repeating units comprise amino acid residues selected from the group consisting of hydrophohic amino acid and glycine residues, wherein the repeatinq units exist in a conformation having a β-turn which comprises A) a polypentapeptide unit of the formula:

and B) a polypentapeptide unit of the formula:

wherein for the above formulas,
I is a peptide-forming residue of L-isoleucine;
P is a peptide-forming residue of L-proline;
G is a peptide-forming residue of glycine;
V is a peptide-forming residue of L-valine; and
wherein X$^1$ and X$^2$ are each PGVG, GVG, VG, G or a covalent bond; Y$^1$ is IPGV, IPG, IP or I or a covalent bond; Y$^2$ is VPGV, VPG, VP, V or a covalent bond; and n in both formulas an integer from 1 to 200; or n in both formulas is 0, with the proviso that X$^1$ and Y$^1$ together, and X$^2$ and Y$^2$ together constitute a repeating pentapeptide unit, in relative amounts sufficient to adjust the development of elastomeric force of the bioelastomer to a predetermined temperature.

It should be noted that bioelastomeric polypeptide chains containing either one or both of the above pentapeptide repeating units can be synthesized using any of the pentapeptide "monomers" that are permutations of the basic sequence. However, if the polymer is not synthesized using the pentapeptide "monomers", but rather is synthesized by sequential adding of amino acids to a growinq peptide, such as in the case of an automatic peptide synthesizer, the designation of the repeating unit is somewhat arbitrary. For example, the peptide H-V(PGVGVPGVGVPGVGVPGVGV)P-OH can be considered to consist of any of the following repeating units and end groups: H-(VPGVG)$_4$-VP-OH, H-V-(PGVGV)$_4$-P-OH, H-VP-(GVGVP)$_4$-OH, H-VPG-(VGVPG)$_3$-VGVP-OH, or H-VPGV-(GVPGV)$_3$-GVP-OH, for example.

Furthermore, it is entirely possible and within the ambit of the present invention that mixed repeating units such as those of the formula -VPGVGIPGVG-$_n$ can be incorporated into the bioelastomers of the present invention.

Synthesis of the elasticity promoting and modifying segments, which are incorporated into the final elastomeric polypeptide, is straightforward and easily accomplished by a peptide chemist. The resulting intermediate peptides qenerally have the structure, B$^1$-(repeating unit)$_n$-B$^2$, where B$^1$ and B$^2$ represent any chemically compatible end group on the amino and carboxyl ends of the molecule, respectively, and n is an integer of from 2 to about 200. Of course, when B$^1$ is -H and B$^2$ is -OH, and n is 1, the compound is either the pentapeptide H-VPGVG-OH or H-IPGVG-OH. When n is greater than 1, the compound intermediate is a polypentapeptide. The same will hold true when utilizing tetrameric repeating units in the present bioelastomers.

It should be noted that the term "hydrophobic amino acid" refers to amino acids which have appreciably hydrophobic R groups as measured on a hydrophobicity scale generated by measuring the relative solubilities of the amino acids in organic solvents, or by measuring their relative effect on surface tension. In this respect, see *Arch. Biochem. Biophy*, Bull and Breese, Vol. 161, 665-670 (1974). By this method, all amino acids which are more hydrophobic than glycine may be used. More specifically, preferable hydrophobic amino acids are Ala, Val, Leu, Ile and Pro.

It should also be noted that it is entirely possible that one or more amino acid residues or segments of amino acid residues not present in the normal pentapeptide or tetrapeptide sequence may be interspersed within a polypentapeptide or polytetrapeptide portion of an elastomeric polypeptide chain.

The bioelastomers of the present invention, regardless of the particular functional repeating unit incorporated therein, may have these repeating units incorporated either in the form of block or random copolymers as long as the desired shift in temperature of elastomeric force development of the bioelastomer is obtained. As noted above, by considering the transition temperatures and temperatures of elastomeric force development for two PPP or PTP analogs, or even for a PPP analog and a PTP analog, it is possible to attain a desired intermediate transition temperature and temperature of elastomeric force development by directly correlating the molar ratios of each analog component therewith. For example, a 50/50 molar ratio of two analog components would give rise to a bioelastomer "copolymer" having a transition temperature and temperature of elastomeric force development approximately in between those of the analog components.

Additionally, it is also noted that the elastomeric units used in conjunction with all aspects of the present invention, i.e., whether the repeating unit is PPP, PTP or analogs thereof, may also comprise those described in U.S. Pat. Nos. 4,187,852; 4,474,851; 4,500,700; 4,589,882, 4,605,413 and 4,693,718 and U.S. patent applications Ser. Nos. 853,212, 900,895 and 062,557 all of which patents and patent applications are incorporated herein in their entirety.

Furthermore, it is also noted that while in most instances all of the bioelastomers of the present invention have a value of n of up to 200, if desired, n can be as high as 5,000.

The aspect of the present invention with respect to PPP and analogs thereof will now be illustrated by Examples, which are provided only for tee purpose of illustration and are not intended to limit the present invention.

EXAMPLES

Peptide Synthesis

The synthesis Ile$^1$-PPP was carried out by the classical solution methods as shown in Scheme I.

In the following Examples, the following abbreviations will be used: Boc, tert-butyloxycarbonyl; Bzl, benzyl; DMF, dimethylformamide; DMSO, dimethylsulfoxide; EDCI, 1-(3-dimethylaminopropyl,-3-ethyl-carbodiimide; HOBt, 1-hydroxybenzotriazole; IBCF, isobutylchloroformate; NMM, N-methylmorpholine; ONp, p-nitrophenylester; TFA, trifluoroacetic acid; PPP, (VPGVG)$_n$; Ile$^1$-PPP, (IPGVG)$_n$; V, valine; I, isoleucine; P, proline; G, glycine.

Scheme I
Synthesis of H—(Gly—Val—Gly—Ile—Pro)$_n$—OH

| Gly | Val | Gly | Ile | Pro | | |
|---|---|---|---|---|---|---|
| | | | Boc—OH | H—OBzl | | |
| | | | Boc— | i OBzl | (I) | |
| Boc— | (II) | —OH | H— | ii OBzl | | |
| Boc— | | | | iii OBzl | (III) | |
| Boc— | | | | iv OH | (IV) | |
| Boc— | | | | v ONp | (V) | |
| H— | | | | vi ONp | | |
| H—( | | | | vii )$_n$—OH | (VI) | | i IBCF/HOBt;
ii HCl/Dioxane;
iii EDCI/HOBt;
iv H2-Pd/C;
v Bis(p-nitrophenyl)carbonate;
vi TFA;
vii DMSO-NMM The sequence of the starting pentamer for polymerization is preferably Gly-Val-Gly-Ile-Pro rather than Ile-Pro-Gly-Val-Gly, because the permutation with Pro as the C-terminal amino acid produces high molecular weight polymers in better yields. The approach to the synthesis entailed coupling the tripeptide Boc-GVG-OH (II) with H-IP-OBzl, each in turn being synthesized by the mixed anhydride methodology of J. R. Vaughan et al, *J. Am. Chem. Soc.*, 89, 5012 (1967). The possible formation of the urethane as a by-product during the reaction of Boc-Ile-OH with H-Pro-OBzl by the mixed anhydride method was avoided by carrying out the reaction in the presence of HOBt. The dipeptide was also prepared using EDCI for confirmation of the product. The pentaoeptide benzylester (III) was hydrogenated to the free acid (IV) which was further converted to the p-nitrophenylester (V) on reacting with bis(p-nitrophenyl)carbonate. On removing the Boc-group, a one molar solution of the active ester in DMSO was polymerized in the presence of 1.6 equiv. of NMM. The polypeptide was dialyzed against water using a 50,000 dalton cut-off dialysis tubing and lyophilized. The purity of the intermediate and final products was checked by carbon-13 nuclear magnetic resonance, elemental analyses and thin layer chromatography (TLC).

Elemental analyses were carried out by Mic Anal, Tuscon, Ariz. All amino acids are of L-configuration except for glycine. Boc-amino acids were purchased from Bachem, Inc., Torrance, Calif. HOBt was obtained from Aldrich Chemical Co., Milwaukee, Wis. TLC was performed on silica gel plates purchased from Whatman, Inc., Clifton, N.J. in the following solvent systems: $R_f^1$, CHCl$_3$ (C):CH$_3$OH(M):CH$_3$COOH(A), 95:5:3, $R_f^2$, CMA (85:15:3); $R_f^3$, CMA (75:25:3); $R_f^4$, CM (5:1). Melting points were determined with a Thomas Hoover melting point apparatus and are uncorrected.

Boc-Ile-Pro-OBzl (mixed anhydride method) (I): Boc-Ile-OH (12.01 @, 0.05 mole) in DMF (50 ml) was cooled to 0° C. and NMM (5.49 ml) was added. After cooling the solution to −15° C. isobutylchloroformate (6.48 ml) was added slowly while maintaining the temperature at −15° C. and stirred for 10 minutes at which time HOBt (7.65 g) was added and stirring was continued for additional 10 minutes. A pre-cooled solution of HCL-H-Pro-OBzl (12.09 g. 0.05 mole) in DMF (50 ml) and NMM (5.49 ml) was added to the above solution and the completeness of the reaction was followed by TLC. The reaction mixture was poured into a cold saturated NaHCO$_3$ solution and stirred for one hour. The peptide was extracted into CHCl$_3$ and washed with acid and base (0.5N NaOH to remove HOBt), and on evaporting the solvent the product was obtained as an oil in 92% yield. $R_f^1$, 0.65. Anal. Calcd. for C$_{23}$H$_{34}$N$_2$O$_5$: C 66.00, H 9.19, N 6.69%. Found: C 65.58, H 8.28, N 7.13%.

Boc-Ile-Pro-OBzl (using EDCI): Boc-Ile-OH (7.20 g, 0.03 mole) and HOBt (5.05 g, 0.033 mole) in DMF (30 ml) was cooled to −15° C. and EDCI (6.32 g, 0.033 mole) was added. After stirring for 20 minutes, a pre-cooled solution of HCl-H-Pro-OBzl (7.25 g; 0103 mole) in DMF (30 ml) and NMM (3.3 ml) was added and stirred overnight at room temperature. After evaporating DMF, the residue was taken into CHCl$_3$ and extracted with 20% citric acid and 0.5N NaOH. The solvent was removed and the product was obtained as an oil in almost quantitative yield which was identical to the product obtained by the mixed anhydride method.

Boc-Gly-Val-Gly-Ile-Pro-OBzl (III): Boc-GVG-OH (II) (20) (5.6 g, 0.017 mole) was coupled with H-IlePro-OBzl (6.7 g, 0.019 mole) (obtained by deblocking I with HCl/Dioxane) in the presence of EDCI (3.65 g, 0.019 mole) and HOBt (2.9 g, 0.019 mole) and the product was worked up as described above to obtain 8.8 g of III (yield: 82.4%), m.p. 107°–108° C. (decomp.) $R_f^1$, 0.44; $R_f^2$, 0.75. Anal. calcd. for C$_{32}$H$_{49}$N$_5$O$_{10}$: C 60.83, H 7.81, N 11.08%. Found: C 61.12, H 8.06, N 11.06%.

Boc-Gly-Val-Gly-Ile-Pro-OH (IV): III (7.8 g, 0.0123 mole) was taken in acetic acid (80 ml) and hydrogenated in the presence of 10% Pd-C (1 g) at 40 psi. After filtering the catalyst with the aid of celite, the solvent was removed under reduced pressure, triturated with ether, filtered, washed with ether then pet. ether and dried to obtain 6.5 g of the product (yield: 97.3%), m.p. shrinks at 127° C. and decomp. at 3 145° C. $R_f^3$, 0.24; $R_f^4$, 0.11. Anal. Calcd. for $C_{25}H_{43}N_5O_{10}\cdot\frac{1}{2}H_2O$: C 54.52, H 8.05, N 12.7%. Found: C 54.32, H 8.02, N 12.59%.

Boc-Gly-Val-Gly-Ile-Pro-ONp (V): IV (5.41 g, 0.01 mole) in pyridine (40 ml) was reacted with bis(pnitrophenyl)carbonate (4.56 g, 0.015 mole) following the completeness of the reaction by T@C. Pyridine was removed; the residue was taken into $CHCl_3$ and extracted with acid and base. The p-nitrophenyl ester obtained was chromatographed over a silica gel (200–400 mesh) column. After initial washing with $CHCl_3$, 4.8 g of V was obtained when eluted with 35% acetone in $CHCl_3$ (yield: 71.4%), m.p. 97°–100° C. $R_f^4$, 0.72; $R_f^4$, 0.75; Anal. Calcd. for $C_{31}H_{46}N_6O_{12}\cdot2H_2O$: C 53.28, H 7.21, N 12.02%. Found: C 53.76, H 6.83, N 12.01%.

H-(Gly-Val-Gly-Ile-Pro)$_n$-OH(VI): The Boc-group was removed from V (3.8 g, 0.0057 mole) by reacting with TFA (35 ml) for 45 min. TFA was removed under reduced pressure, triturated with ether, filtered, washed with ether, pet. ether and dried. The TFA salt (3.3 g, 0.0049 mole) in DMSO (4.9 ml) was stirred for 14 days in the presence of NMM (0.86 ml, 0.0078 mole). After diluting with water in the cold, the polypeptide was dialyzed using a 50 kD cut-off dialysis tubing changing the water daily for 15 days. The retentate was lyophilized to obtain 1.81 g of the Ile$^1$-polypentapeptide (yield: 88%). The carbon-13 NMR spectrum is presented in FIG. 1 along with that of the regular polypentapeptide for comparison.

Temperature Profiles for Coacervation

The temperature dependence for aggregation of the polypentapeptide is followed as the development of turbidity at 300 nm using a Cary 14 spectrophotometer. The sample cell is placed within a chamber vibrating at 300 Hz in order to facilitate equilibrium and to keep the aggregates from settling. The scan rate is 30° C./hour and the temperature was controlled with a Neslab ETP-3 programmer and monitored with an Omega 199A thermocouple monitor placed at the cell. The turbidity as a function of temperature provides a temperature profile for coacervation which is found to be concentration dependent. As the concentration is raised, the profile shifts to lower temperatures until further increases in concentration cause no further lowering of the temperature for aggregation. This defines the high concentration limit. The temperature for the onset of coacervation at the high concentration limit coincides with the temperature for the onset of the transition within the coacervate itself, even when there is no appreciable change in water content of the coacervate. The temperature for the midpoint of the temperature profile for the high concentration limit has been shown to correlate with the molecular weight of the polypentapeptide. When the midpoint is 25° C. for the PPP, the molecular weight is close to 100,000 daltons as calibrated by dialysis. For the Ile$^1$-PPP a with a midpoint of 9° C., the molecular weight is greater than 50,000 daltons, as the syntheic polypeptide was retained by a 50,000 daltons dialysis membrane. The dialysis was carried out at 4° C. where the Ile$^1$-PPP is in solution.

Circular Dichroism Measurements

The circular dichroism studies were carried out on a Cary 60 spectropolarimeter equipped with a Model 6001 CD accessory modified for 330 Hz modulation of the left and right circularly polarized light. A concentration of 0.025 mg Ile$^1$-PPP/ml of doubly distilled water was characterized in a 10 mm path length cell. The low concentration was used to keep the size of the aggregate sufficiently small as not to cause light scattering distortions of the CD spectra. Even at this low concentration with this more hydrophobic polypentapeptide, above 35° C. the size of the aggregates was sufficient to cause particulate distortions as was apparent with the red shifting and dampening of the long wavelenqth negative band. The temperature was controlled and monitored from the cell as for the temperature profiles for coacervation.

Formation of the Elastomeric Matrix

In preparation for $\gamma$-irradiation cross-linking (the means of forming the elastomeric matrix), 130 milligrams of peptide Ile$^1$-PPP were dissolved in 220 milligrams of water in a cryotube. The sample was then shear oriented at 0° C. in a previously described pestle-cryotube arrangement. Gamma-irradiation was carried out at the Auburn University Nuclear Science Center at a dose rate of approximately 8,000 Roentgen/min and for sufficient time to achieve a $20 \times 10^6$ radiation absorbed dose (20 Mrad).

Thermoelasticity Studies

Thermoelasticity studies were carried out on a stress-stain instrument built in this Laboratory. The sample is mounted in two Delrin clamps. The top clamp is attached to a Statham UTC strain-gauge and the assembly is fixed. The bottom clamp is attached to a moving platform driven by a variable speed motor. Both clamps are enclosed in a thermostated water jacket. An inner chamber contains the solvent in which the elastomer is immersed which in this case is doubly distilled water. The sample was fixed in the top clamp and equilibrated in water at 60° C. for about an hour. The strain-gauge signal conditioner was balanced for zero force and the bottom clamp was attached to the sample. The sample was left to set overnight at room temperature. The bottom clamp was then adjusted for zero force and the distance between the clamps was measured. The elastomer was elongated to 40% extension at 5° C. and elastomeric force was then determined as a function of temperature. Equilibrium time to achieve constant force at a given temperature was typically twenty-four hours. Force measurements were made in 2° C. increments through the sharp rise in force an 5° C. increments at higher temperatures.

RESULTS

Temperature Profiles for Coacervation The Ile$^1$-PPP can be dissolved in water on standing below 8° C. On raising the temperature of the solution above 8° C., the solution becomes cloudy; on standing at the elevated temperature settling occurs and a viscoelastic phase forms in the bottom of the vial; on placing the vial in an ice bath the cloudiness immediately clears and the viscoelastic phase readily dissolves. Thus the Ile$^1$-PPP coaceravates when dissolved in water. The temperature profiles for coacervation (turbidity profiles) shift with different concentrations. As the concentration is raised, the temperature profile shifts to lower temperature. At 40 mg/ml, the high concentration limit (i.e, the lower concentration for which further increases in concentration cause no further lowering of the temperature for the onset of aggregation), the midpoint for the temperature profile for coacervation of Ile$^1$-PPP is 9° C.

Notably, the simple addition of a CH$_2$ to the 409 dalton repeating unit causes the onset of aggregation to shift to lower temperatures by 16° C. Observing that curve f (0.1 mg Ile$^1$-PPP,/ml) and curve k (1.0 mg PPP/ml) are comparable with respect to the high concentration limits for each high molecular weight polymer suggests that the size of the aggregate for Ile$^1$-PPP is greater for a given concentration than it is for a comparable concentration of PPP. This will be relevant to comparisons made in the circular dichroism data.

Circular Dichroism

The circular dichroism curves were measured for Ile$^1$-PPP in water (0.025 mg/ml) at 2° C. and at 35° C. The low concentration was chosen in order that the size of the aggregate formed on association at 35° C. would have limited particulate distortions in the CD spectrum. At low temperature there is a large negative band near 195 n. Such a negative band is characteristic of disordered proteins and polypeptides, though a standard value for this negative peak for complete disorder is $-4 \times 10^4$ rather than the observed value of $-1.2 \times 10^4$. Also the negative band near 220 nm, rather than zero ellipticity or a positive band which are taken is indicative of complete disorder, suggests elements of order at low temperature. The decrease in intensity of the negative CD band near 195 nm on raising the temperature of Ile$^1$-PPP in water indicates an increase in intramolecular order on raising the temperature, that is, there is an inverse temperature transition in an aqueous system. This indicates that hydrophobic interactions are developing as the ordered state develops. The intramolecular increase in order begins just above 0° C. and is complete by about 30° C. for a concentration of 0.025 mg/ml. The transition would have been complete at a lower temperature (the transition would have been sharper) if the CD data could have been obtained at higher concentration without significant particulate distortion. Experimentally it can be demonstrated that Ile$^1$-PPP and PPP have essentially identical conformations below the onset temperature for the transition and that they have essentially identical conformations after the transition is mostly completed. Thus while maintaining essentially identical conformations, which is assisted by the retention of β-branching, the addition of a CH$_2$ moiety lowers the transition toward increased order by about 15° C.

Characterization of Elasticity

The elastic (Young's) modulus determined for 20 MRAD cross-linked Ile$^1$-PPP coacervate was $4 \times 10^5$ dynes/cm$^2$ which is within the range of values obtained for 20 Mrad cross-linked PPP. The range of values is due to variable vacuolization occurring during γ-irradiation which makes difficult accurate measurement of cross-sectional area. It should be appreciated, however, that γ-irradiation causes no detectable polymer breakdown when measured by carbon-13 and nitrogen-15 NMR.

The temperature dependence of elastomeric force for an elastomeric band of Ile$^1$-PPP at 40% elongation is now considered. A near zero elastomeric force is measured at 8° C.; on raising the temperature there is a dramatic, an abrupt increase in elastomeric force. Full force is reached by 25° C. and becomes essentially constant with further increases in temperature. A similar dramatic rise in elastomeric force with increase in temperature is observed for 20 Mrad cross-linked PPP coacervate at 60% extension but this curve Is displaced about 15° C. to higher temperatures. Using three different physical methods it can be shown that the addition of a CH$_2$ moiety (the replacement of Val by Ile) shifts the transition to lower temperatures by 15° C. without changing the conformation of the polypentapeptide before and after the transition. While the previously reported data on the naturally occurinq PPP of elastin demonstrate a correlation of increased structural order with increased elastomeric force, the Ile$^1$-PPP data with the transition shifted by 15° C. appear to confirm an obligatory coupling of increased order with increase elastomeric force.

In fact, the correlation of increased order with increased elastomeric force is seen with the PPP. When the transition is shifted to lower temperatures, as in Ile$^1$-PPP, the development of elastomeric force faithfully shifts to lower temperatures. There appears in such elastomeric polypeptides to be a strict coupling between increasing order and increasing elastomeric force; and the molecular structure provides an understanding as to how this can occur. The similar conformations of PPP and Ile$^1$-PPP and the similar elastic moduli for the two polymers indicate that these do not appear to be factors in the evolutionary retention of (VPGVG)$_n$. What is now clear is that even the subtle addition of a-CH$_2$-moiety, for example, while having little effect on the stereochemistry of rather nonexacting, nonrestricting hydrophobic associations, has a significant effect on the thermodynamics. The larger clathrate-like cage of water surrounding the Ile side chain provides a greater $\Delta S$ as the more-ordered water surrounding the side chain becomes less ordered bulk water such that in the transition $\Delta H = T \Delta S$ at a lower temperature. By means of calorimetry, the $\Delta H$ for PPP has been estimated at 2 cal/gram which is less than 1 kcal/mole of pentamers. Thus, the increase in entropy change need only be about 5% to cause the temperature of the transition to decrease about 15° C. from 298° K. to 283° K. Utilizing known hydrophobicity scales for amino acids, the hydrophobicities given in a free energy of transfer scale of kcal/mole, are $-4.10$ for VPGVG and $-5.38$ for IPGVG. While the extent of the hydrophobicity that is utilized is expected to depend on the stereochemistry of the more-ordered polypeptide state, it would appear that not all of the total potential effect is actually realized.

The above-described hydrophobic effect upon transition temperatures is also supported by the elastin polytetrapeptide, (Val$^1$-Pro$^2$-Gly$^3$-Gly$^4$)$_n$. That is, it has also been discovered that high molecular weight PTP undergoes a reversible temperature elicited aggregation with an onset of aggregation at 48° C., rather than 24° C. as for high molecular weight PPP.

However, it has also been found that the inverse temperature transition for PTP is only complete at about 70° C. Moreover, this high temperature of transition appears to be explained by considering the lower hydrophobicity of PTP as compared to PPP.

For example, utilizing the Bull-Breese hydrophobicity scales with the hydrophobicity of the Gly residue taken as zero, the free energy of transfer for the pentamer, VPGVG, would be $-4100$ cal/mole whereas that of the tetramer, VPGG, would be −2540 cal/mole. Thus, if hydrophobicity of the repeating unit is the determining factor, then the inverse temperature transition for the PTP would be at a higher temperature than that of the PPP. Furthermore if the inverse temperature transition (the increase in intramolecular order) is required for the development of elastomeric force, then the temperature dependence of elastomeric force of the PTP matrix would be expected to show a similar shift to higher temperature relative to that of the PPP matrix.

This inverse temperature transition is actually centered at near 50° C. for PTP, shifted some 25° C. higher than that of PPP. For Ile$^1$-PTP, it is shifted some 30° C. lower in temperature than that of PTP. Also, it has been found that the development of elastomeric force upon raising the temperature is similarly shifted about 25° C. higher for the PTP matrix (20 Mrad crosslinked) as compared to the PPP matrix (20 Mrad crosslinked).

Accordingly, in view of the above, it is now possible, by selecting the appropriate combination of PTP and PPP matrices or analogs thereof of the present invention to shift the transition temperature of a bioelastomer containing elastin PTP, PPP and analogs thereof and PHP over a range of about 75° C. Furthermore, whereever this transition would occur in the range of about −25° C. for Phe$^1$-PPP in water/ethylene glycol or about 50° C. for PTP, in water, for example, there is a large change in elastomeric force which accompanies a relatively small change in temperature.

Thus, it is now possible to provide bioelastomers having incorporated therein repeating units having decreased hydrophobicity, such as-(VPGG)$_n$-.

In particular, in accordance with the present invention, is also provided a bioelastomer containing elastomeric units comprising tetrapeptide, or pentapeptide or units thereof modified by hexapeptide repeating units and mixtures thereof, wherein the repeating units comprise amino acid residues selected from the group consisting of hydrophobic amino acid and glycine residues, wherein said repeating units exist in a conformation having β-turn which comprises a tetrapeptide of the formula:

—X$^3$—(VPGG)$_n$—Y$^3$— 

wherein X$^3$ is PGG, GG, G or a covalent bond;
Y$^3$ is VPG, VP, V or a covalent bond; and
V is a peptide-producing residue of L-valine;
P is a peptide-producing residue of L-proline; and
G is a peptide-producing residue of glycine; and n is an integer from 1 to 200, or n is 0, with the proviso that X$^3$ and Y$^3$ together constitute a repeating tetrameric unit in an amount sufficient to adjust the development of elastomeric force of the bioelastomer to a predetermined temperature.

Moreover, the present invention also further provides a bioelastomer containing elastomeric units comprising tetrapeptide, or pentapeptide or units thereof modified by hexapeptide repeating units and mixtures thereof, wherein the repeating unit comprises amino acid residues selected from the group consisting of hydropholic amino acid and glycine residues, wherein said repeating units exist in a conformation having a β-turn which comprises A) a polypentapeptide of the formula:

—X$^1$—(IPGVG)$_n$—Y$^1$— 

wherein X$^1$, Y$^1$, P, G, I, V and n are as defined above; and

B) a polypentapeptide of the formula:

—X$^2$—(VPGVG)$_n$—Y$^2$— 

wherein X$^2$, Y$^2$, P, G, V and n are as defined above; or

C) a polytetrapeptide of the formula:

—X$^3$—(VPGG)$_n$—Y$^3$— 

wherein X$^3$, Y$^3$, P, G, V and n are as defined above in relative amounts sufficient to adjust the development of elastomeric force of said bioelastomer to a predetermined temperature.

In accordance with the present invention are also provided PTP analogs, such as Ile$^1$-PTP, which are analogous to the various PPP analogs described above. In fact, any PTP-analog can be used in the preparation of the present bioelastomers which suffices to attenuate the hydrophobicity of the functional repeating unit, such as -IPGG-$_n$, while retaining the elasticity of the bioelastomer. Accordingly, in view of the principles set out above, one skilled in the art would, in view of this disclosure, be able to ascertain other PTP analogs which can be used advantageously in accordance with the present invention.

Thus, in accordance with the present invention is also provided a bioelastomer containing elastomeric units comprising tetrapeptide, or pentapeptide or units thereof modified by hexapeptide repeating units and mixtures thereof, wherein the repeating units comprise hydrophobic amino acid and glycine residues, wherein the repeating units exist in a conformation having a β-turn which comprises a tetrapeptide of the formula:

—X$^4$—(IPGG)$_n$—Y$^4$— 

wherein X$^4$ is PGG, GG, G or a covalent bond;
Y$^4$ is IPG, IP, I or a covalent bond; and
I is a peptide-producing residue of L-isoleucine;
P is a peptide-producing residue of L-proline; and
G is a peptide-producing residue of glycine; and n is an integer from 1 to 200, or n is 0, with the proviso that X$^4$ and Y$^4$ together constitute a repeating tetrameric unit, in an amount sufficient to adjust the temperature of which the elastomeric force of the bioelastomer develops.

Of course, also within the ambit of the present invention are bioelastomers having the above-recited structural features, but which have any combination of the repeating units —IPGVG)$_n$, —VPGVG)$_n$, —VPGG)$_n$, —IPGG)$_n$ or other analogs thereof, such as Ala$^3$-PPP or Phe$^1$-PPP.

In fact, the present invention includes, in general, all bioelastomers containing elastomeric units comprising tetrapeptide, or pentapeptide or units thereof modified by hexapeptide repeating units and mixtures thereof, wherein the repeating units comprise hydrophobic amino acid residues and glycine residues, wherein the repeating units exist in a conformation having a β-turn which comprises a tetrapeptide or pentapeptide unit or repeating unit thereof, in an amount sufficient to adjust the development of elastomeric force of said bioelastomer to a predetermined temperature, with the proviso that the elasticity of the bioelastomer is retained.

However, in order to clarify the various aspects of the present invention relating to PTP, the following Examples and discussion are provided. Of course, the Examples are for purposes of illustration only and are not intended to limit the present invention.

EXAMPLES

Peptide Synthesis

General Approach: The synthesis of polytetrapeptide, (VPGG)$_n$, can be achieved using any of the following permutations as the starting tetramer unit: Val-Pro-Gly-Gly, Gly-Val-Pro-Gly, Gly-Gly-Val-Pro, or Pro-Gly-Gly-Val. The first sequence (VPGG) was used in this laboratory both with the pentachlorophenyl ester (OPcp) activation and with the p-nitrophenyl ester (ONp) activation methods, and the latter method yielded polymer of significantly higher molecular weight. The sequence (GVPG) was utilized with —OPcp activation but no mention was made about the size of the polymer. In synthesizing the polypentapeptide, (VPGVG)$_n$, using different permutations of the pentamer unit with different activating groups for polymerization, it was observed that the pentamer having Pro as the C-terminal amino acid and —Onp for activation gave high molecular weight polymers. Similar results have been experienced in the case of the preparation of polyhexapeptide, (VAPGVG)$_n$. Hence, a similar approach was determined to be reasonable in the case of PTP also, i.e., sequence (GGVP) with —ONp activation. For comparison, H-VPGG-ONp, H-GVPG-ONp and H-GGVP-ONp were all tried for polymerization. As expected, the latter tetramer sequence gave a very high molecular weight polymer when determined by the TPrstudies and here is described the synthesis of this latter material as shown in the Scheme II. The sequence (PGGV) was not attempted because it has an optically active and bulky amino acid, Val, at its C-terminal.

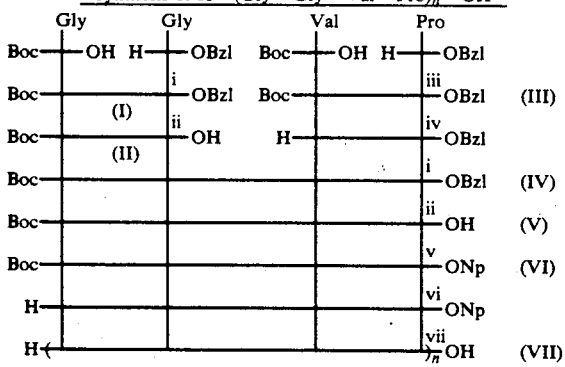

Scheme II
Synthesis of H—(Gly—Gly—Val—Pro)$_n$—OH i EDCI-HOBt;
ii H2-Pd/C;
iii IBCF-HOBt;
iv HCl/Dioxane;
v Bis(p-nitrophenyl)carbonate;
vi TFA;
vii DMSO-NMM Boc-GG-OBzl (I) was prepared using EDCI for coupling and was hydrogenated to give the acid (II). Boc-VP-OBzl (III) was synthesized by the mixed anhydride method in the presence of HOBt, deblocked, and coupled with II using EDCI-HOBt to obtain Boc-GGVP-OBzl (IV). After hydrogenating to the acid, V, it was converted to —ONp (VI) by reacting with bis-(p-nitrophenyl)carbonate. After removing the Boc-group, the active ester was polymerized, dialyzed against water using a 50,000 molecular weight cut-off dialysis tubing and lyophilized. The intermediate and the final products were checked by carbon-13 nuclear magnetic resonance, thin-layer chromatography (TLC) and elemental analyses.

Details of Syntheses: Valine and Proline are of L-configuration. Boc-amino acids were purchased from Bachem, Inc., Torrance, CA. HOBt was obtained from Aldrich Chemical Co., Milwaukee, WI, and Bio-sil silica gel (200–400 mesh) was purchased from Bio-Rad Laboratories, Richmond, CA. TLC plates were obtained from Whatman, Inc., Clifton, NJ and the following solvent systems were used for determining the homogeneity of the products: $R_f{}^1$, CHCl$_3$(C):MeOH (M):CH$_3$COOH (A), 95:5:3; $Rf{}^2$, CMA (85:15:3); $R_f{}^3$, CMA (75:25:3); $R_f{}^4$, CM (5:1). Elemental analyses were carried out by Mic Anal, Tuscon, AZ. Melting points were determined with a Thomas Hoover melting point apparatus and are uncorrected.

Boc-Gly-Gly-OBzl (I): Boc-Gly-OH (17.52 g, 0.1 mole) in a mixture of CHCl$_3$ (50 ml) and acetonitrile (50 ml) was cooled to $-15°$ C. and EDCI (19.17 g, 0.1 mole) was added and stirred for 20 minutes. To this, a pre-cooled solution of H-Gly-OBzl.tosylate (37.1 g, 0.11 mole), NMM (12.09 ml, 0.11 mole) in CHCl$_3$(100 ml) was added and stirred overnight at room temperature. After removing the solvent, the residue was taken in CHCl$_3$ and extracted with acid and base. Chloroform was removed under reduced pressure, triturated with pet. ether, filtered, washed with pet. ether and dried to obtain 30.2 g of I (yield: 93.7%), m.p. 82°–83° C. $R_f{}^2$, 0.52; $R_f{}^4$, 0.82. Anal. Calcd. for C$_{16}$H$_{22}$N$_2$O$_5$: C, 59.61; H, 6.88; N, 8.69%. Found C, 59.43; H, 6.88; N, 8.35%

Boc-Gly-Gly-OH (II): I (10 g, 0.31 mole) in acetic acid (100 ml) was hydrogenated at 40 psi in the presence of 10% Pd-C catalyst (1 g). The catalyst was filtered with the aid of celite and solvent removed under reduced pressure. The residue was triturated with EtOAC, filtered, washed with EtOAC, pet. ether and dried to yield 6.3 g of II (yield: 87.5%), m.p. 118°–120° C. (decomp.). $R_f{}^2$, 0.28; $R_f{}^3$, 0.44. Anal. Calcd. C$_9$H$_{16}$N$_2$O$_5$.H$_2$O: C, 43.19; H, 7.25; N, 11.19%. Found: C, 43.53; H, 7.40; N 10.90%.

Boc-Gly-Gly-Val-Pro-OBzl (IV): III (6.0 g, 0.0148 mole) (39) was deblocked with HCl/Dioxane and solvent removed under reduced pressure. The residue was triturated with ether, filtered, washed with ether, then pet. ether and dried. A very hygroscopic material was obtained (4.2 g, 0.0123 mole) which was coupled in DMF with II (2.86 g, 0.0123 mole) in the presence of 10% excess of EDCI (2.60 g) and HOBt (2.07 g). The reaction was worked up as described for I to obtain IV as a white foam in a quantitative yield, no sharp m.p. 54°–62° C. $R_f{}^2$, 0.42; $R_f{}^3$, 0.74. Anal. Calcd. for C$_{26}$H$_{38}$N$_4$O$_7$; C, 60.21; H, 7.38; N, 10.80%. Found: C, 60.0; H, 7.46; N, 10.81%.

Boc-Gly-Gly-Val-Pro-OH (V): IV (6.2 g, 0.012 mole) in acetic acid was hydrogenated and worked up as for IIto obtain V quantitatively, no sharp m.p. 74°–83° C. $R_f{}^3$, 0.25; $R_f{}^4$, 0.15. Anal. Calcd. for C$_{19}$H$_{32}$N$_4$O$_7$: C, 51.10: H, 7.67; N, 12.54%. Found: C, 51.28: H, 7.50 N, 12.38%.

Boc-Gly-Gly-Val-Pro-ONp (VI): V (5.3 g, 0.0123 mole) in pyridine (30 ml) was reacted with bis(p-nitrophenyl)carbonate (5.64 g, 0.0185 mole). After removing the solvent, the residue was taken in CHCl$_3$ and extracted with acid and base. The peptide was chromatographed over a silica-gel column and eluted with 35% acetane in CHCl₃ after initially eluting with CHCl₃, to obtain 4.7 g of VI (yield: 69.2%), no sharp 2 m.p. 74°–79° C. $R_f^2$, 0.76; $R_f^4$,0.75. Anal. Calcd. for $C_{25}H_{35}N_5O_9 \cdot \frac{1}{2}H_2O$: C, 53.75; H, 6.49; N, 12.53%. Found: C, 53.69; H, 6.44; N, 12.34%.

H-(Gly-Gly-Val-Pro)$_n$-OH (VII): VI (4.5 g, 0.0082 mole) in CHCl₃ (20 ml) was treated with TFA (35 ml) for 30 minutes and solvent removed under reduced pressure. The residue was triturated with ether, filtered, washed with ether, then with pet. ether and dried. The TFA salt (3.9 g, 0.0069 mole) in DMSO (7.6 ml) and NMM (1.22 ml, 1.6 equiv) was stirred for 14 days. After diluting with cold water, the polymer was dialyzed in a 50 kD cut-off dialysis tubing, chanqing water daily for 15 days, and the retentate was lyophilyzed to yield 1.65 g of the polytetrapeptide (yield: 77%). A carbon-13 NMR spectrum of the polymer was used to verify the synthesis of the desired product.

Temperature Profiles for Coacervation Polypeptide

Polypeptide coacervation in water is reversible aggregation to form a new phase with a distinct composition. Association occurs on raising the temperature, disassociation on lowering the temperature. The process of coacervation was followed by monitoring the turbidity as a function of temperature using a Cary 14 spectrophotometer set at 300 nm, a Neslab ETP-3 temperature programmer with a 30° C./hour scan rate and an Omega 199A thermocouple monitor. The sample cell was placed in a vibrating chamber (300 Hz) to keep the aggregates from settling and to facilitate equilibrium. The temperature profiles for coacervation are concentration dependent. Dilution from a high concentration, after the high concentration limit is reached (approximately 40 mg/ml for high molecular weight elastomeric polypeptides), results in a shift of the turbidity profile to higher temperature.

Circular Dichroism Measurements

A Cary 60 spectropolarimeter equipped with a Model 6001 circular dichroism accessory with 330 Hz modulation of the left and right circular polarized beams was used to determine the circular dichroism patterns of 5 mg PTP in one ml of deionized-distilled (quartz immersion heater) water. Because of the smaller size or the relative transparency of the PTP aggregates (as with the cross-linked PTP matrix with a relatively small change in refractive index between solution and matrix) when compared to that of the PPP system, it was possible to use the 5 mg/ml concentration for the CD studies without being compromised by light scattering (particulate) distortions of the CD spectra. This is apparent from monitoring the negative band near 220 nm which becomes damped and red-shifted as the particulate distortions become significant.

Preparation of the Cross-linked PTP Matrix

The PTP was prepared for γ-irradiation cross-linking by dissolving 130 milligrams of the peptide in 220 milligrams of water in a cryotube. The material was shear oriented overnight at 40° C. in a previously described pestle-cryotube assembly. The sample was exposed to approximately 8,000 Roentgen/min γ-irradiation at the Auburn University Nuclear Science Center. Exposure was of sufficient time to achieve a 20×10⁶ radiation absorbed dose (20 Mrad).

Thermoelasticity Measurements

Thermoelasticity studies were carried out on a stress-strain apparatus. Clamping of the sample in the holder was done in two stages to prevent damage to the material at the clamp edge. The sample was first gripped lightly with the top clamp, raised to 60° C. while submerged in water within the temperature jacket and allowed to equilibrate for about 2 hours. The measured force consisting of the weight of the sample and grips in water were set to zero. The bottom grip was then attached to the sample and both grips tightened to hold the sample firmly. The bottom clamp was driven as in a stress-strain measurement and stopped at 40% elongation. Force data were recorded in 5° C. steps starting at 70° C. and continuing to 40° C. where the force approached zero.

RESULTS

Temperature Profiles for Coacervation

The polytetrapeptide is soluble in water in all proportions below 40° C. On raising the temperature above 40° C. the solution becomes turbid; on standing settling occurs to form a dense viscoelastic phase called a coacervate. The process is readily reversible; on lowering the temperature cloudiness clears and coacervate readily redissolves. By following the turbidity as a function of temperature, temperature profiles for coaverva-tion are obtained which are concentration dependent. As more concentrated solutions are used, the onset of turbidity occurs at lower temperatures until further increases of concentration cause no further lowering of the temperature for onset of turbidity. The lower concentration above which raising the concentration no further lowers the temperature for onset of turbidity is called the high concentration limit. For this high moelcular weight PTP the high concentration limit is 40 mg/ml as 100 mg/ml gives the same profile. Dilution from 40 mg/ml causes a shift to higher temperature for the onset. The midpoint for the high concentration limit of PTP is 49° C. whereas the value for the high concentration limit of PPP is 25° C. The decreased hydrophobicity of the tetramer results in a 24° C. increase in the temperature required to bring about the hydrophobic interactions attending aggregation.

Circular Dichroism

The CD spectra were measured at 40° C. and 65° C. for 5 mg/ml of PTP in water. At the lower temperature there is a negative band near 220 nm and a second negative band in the 195–200 nm range. This latter band is considered to be indicative of polypeptides with limited order as fully disordered polypeptides are considered to have a negative band near 195 nm with an ellipticity of $-4 \times 10^4$. The lower magnitude of the short wavelength negative band for PTP and the negative band near 220 nm indicate some order in the PTP at 35° C. On raising the temperature the short wavelength negative band decreases in magnitude indicative of a transition toward greater intramolecular order. Interestingly, its midpoint corresponds approximately to the midpoint in the temperature profile for coacervation for a comparable concentration. It is important to note for the PTP that the change in intramolecular order precedes the intermolecular interactions, i.e., begins at a substantially lower temperature than the aggregational process. Thus, the intramolecular ordering of the PTP is shifted to higher temperature due to the decreased hydrophobicity of the tetramer as compared to the pentamer.

Thermoelasticity Data

The temperature dependence of elastomeric force (thermoelasticity data) was measured for 20 Mrad cross-linked PTP at an extension of 40%. Very little elastomeric force was exhibited by this matrix below 40° C. As the temperature is raised above 40° C., however, the elastomeric force develops to a maximal value near 70° C. A 20 Mrad cross-linked PPP matrix exhibited a similar transition but at about 20° to 25° C. lower in temperature. The development of elastomeric force, just as the temperature dependence of coacervation and of ellipticity for the PTP, is shifted by about 25° C. from that of the PPP. These properties are a function of the hydrophobicity of the repeating unit. Of particular interest is the comparison of the ellipticity data for the PTP with the thermoelasticity for the PTP. The transition as followed by ellipticity, which is a measure of intramolecular order, begins in the range 35° to 40° C., and similarly the elastomeric force begins to develop just below 40° C. By both physical measurements the transition is essentially complete by 70° C. There is a close parallel between-increase in intramolecular order and increase in elastomeric force. As the aggregational intermolecular processes, followed by turbidity, do not become significant until nearly 50° C., it appears that the PTP matrix allows a delineation between interamolecular and intermolecular processes as related to origins of elastomeric force.

The structural features of PTP appear to be very similar to those of PPP. For example, it is clear that the same principles are operative as for the PPP. The Type II $Pro^2$-$Gly^3$ $\beta$-turn is dominant secondary structural feature and the ordering process is that of an inverse temperature transition with the optimization of intramolecular hydrophobic interactions as the temperature is raised. The perspective is again an open helix with $\beta$-turn spacers between turns of the spiral and with the Val and Pro side chains providing the intramolecular hydrophobic contacts. The suspended segment will necessarily be shorter and the librational motion will be focused on the $Gly^4$-$Val^1$ peptide moiety. Based on the cyclic conformational correlate there will be approximately 4 tetramers per turn of PTP $\beta$-spiral as opposed to the approximately 3 pentamers per turn for the PPP $\beta$-spiral.

Effect of Repeat Unit Hydrophobicity

That the transitions toward increased elastomeric force are actually inverse temperature transitions dependent on the hydrophobicity of the constituent peptide is apparent from the direction of the shift of the transition on changing the hydrophobicity of the repeating unit. As the repeating unit becomes more hydrophobic, the temperature for the transition shifts to lower values. Using the Nozaki-Tanford-Bull-Breese hydrophobicity scale, the pentamer (VPGVG) would have a free energy for transfer of $-4100$ cal/mole whereas that for the tetramer (VPGG) would be $-2540$ cal/mole. For the transition $\Delta H = T\Delta S$, and for a given $\Delta H$ a higher temperature would be required if the hydrophobicity giving rise to $\Delta S$ were less. The data of FIGS. 7 and 8 show that the decreased hydrophobicity of the tetramer requires a higher temperature for the transition than for the more hydrophobic pentamer. This finding is in accordance with the above-mentioned results obtained with $Ile^1$-PPP. When $(IPGVG)_n$, or $Ile^1$-PPP, is prepared, the $Ile^1$-PPP coacervates; it increases intramolecular order on increasing the temperature and the $Ile^1$-PPP matrix increases elastomeric force on raising the temperature but the transition is shifted to 9° C. The hydrophobicity for this pentamer, (IPGVG), is $-5380$ cal/mole. A comparison of the temperature of the transition for the three polypeptide elastomers and the hydrophobicities of the repeating unit. Not only is the direction of the shift correct but the magnitude of the shift is also approximately correct. It is clear that the inverse temperature transition giving rise to the intramolecular ordering and elastomeric force development is indeed proportional to the hydrophobicity of the repeating unit, and it is the intramolecular process utilizing hydrophobic interactions that is responsible for the development of elastomeric force.

Thus, the bioelastomers of the present invention can encompass a wide variety of functional repeating units in order to provide a wide variation in temperature of elastomeric force development.

For example, the present bioelastomers include those having any of the following repeating units as defined above:

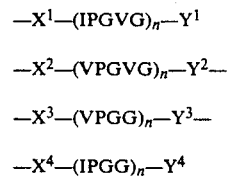

alone or in combination with each other in order to impart to the bioelastomer a capability of developing near maximum elastomeric force at a predetermined temperature.

However, also included with in the ambit of the present invention are all analogs of PPP and PTP and combinations thereof which modulate the hydrophobicity of the PPP and PTP repeating unit or units, without unduly interfering with either the formation of the viscoelastic phase or the librational motion of the polypeptide, i.e., the elasticity.

Other examples of such analogs and combinations thereof are such sequences as:

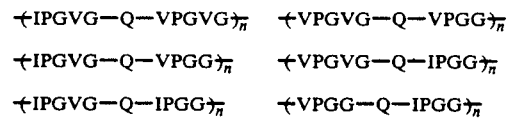

where Q is either a direct covalent bond or an interspersing amino acid residue or residues, which can be any such residue which does not interfere with the elasticity of the polypeptide.

Of course, the repeating pentapeptide sequence, as well as the repeating tetrapeptide sequence can be widely substituted to modify the repeating unit hydrophobicity, as long as the elasticity of the bioelastomer is retained. For example, the incorporated pentapeptide repeatinq unit can be of the general formula:

wherein $R_1$ is a peptide-producing residue selected from the group of Phe, Leu, Ile and Val; $R_2$ is such a residue selected from the group of Ala and gly; and $R_3$ is selected from the group consisting of Phe, Leu, Ile and Val; and n is an integer of from 1 to about 200; and wherein P is a L-proline-producing residue and G is a glycine-producing residue. Thus, "homopolymers" of the above pentameric sequence can be utilized or "copolymers" of the above sequence can be used in conjunction with other repeating units in keeping with this invention.

Also, in general, tetrapeptide repeating units of the formula:

$$-R_1PGG-_n$$

can be utilized, wherein $R_1$ and n are as defined above for the pentameric sequences. These units are incorporated into the present bioelastomers in an amount sufficient to adjust the development of elastomeric force of the bioelastomer to a predetermined temperature.

Generally, in accordance with any of the bioelastomers of the present invention, the bioelastomers can be a "homopolymer" of a functional repeating unit, such as $Phe^1$-PPP, $Ala^3$-PPP $Ile^1$-PPP, or $Ile^1$-PTP; or they can be a "copolymer" of the general formula $-S_a-T_b-n$ wherein either S or T constitutes a functional repeating unit designed to modify or shift the temperature of elastomeric force development of the bioelastomer, while either S or T, whichever is remaining, constitutes another repeating unit of the bioelastomer. As noted, such "copolymers" can be of either the block or random variety, which means that a and b can each be 1 or a larger integer.

Further, for these "copolymers", it is possible, as noted, that more than one functional repeating unit can be used to modify the temperature of elastomeric force development. Thus, both units -S- and -T- in the formula above would be such repeating units, for example, —IPGVG— and —VPGVG—. Of course, each of S and T may be comprised of a subset of repeating units of $S_i$, $S_{ii}$ and $S_{iii}$. For example, three S subsets might be PPP analogs, such as (IPGVG), (FPGVG), where F is the one letter abbreviation for Phe, or (VPAVG).

Each one of the S or T repeating units is preferably incorporated within the molar range of 1–99%. More preferably still, is the incorporation of these units within the molar range of 5–95%. However, the actual molar content of any number of different repeating units is directly proportional to the desired transition temperatures using hydrophobicity scales.

The present bioelastomers contain elastomeric units, in addition to the units which are incorporated to modify the transition temperature, which can be a copolymer of pentapeptide "monomer" units and modifying hexapeptide "monomer" units; tetrapeptide "monomer" units and modifying hexapeptide "monomer" units; or pentapeptide, tetrapeptide, and "monomer" units thereof modified by hexapeptide monomer units.

Finally, although the value of n in all the above formulae is generally 1 to 200, it is possible that n can be 0, with the proviso that the units $X^c$ and $Y^c$ attached to the functional repeating unit, themselves constitute at least one such repeating unit, in an amount sufficient to adjust the elastomeric force development of the bioelastomer to a predetermined temperature. It is also possible for n to have higher values of up to about 5,000 if desired.

III. Reversible Mechanochemical Engines

According to a most important aspect of the present invention it has now been discovered that the elastomeric materials of the present invention may be used advantageously in the design of mechanochemical engines. These will now be discussed making convenient reference to FIG. 7.

A. Engines For the Development of Chemical Gradients

As noted above, the mechanochemical engines of the present invention may be used to convert mechanical work to chemical work. Several examples of this aspect of the present invention will now be described in developing chemical gradients.

First, mechanical stretching of the present elastomeric materials can be used to increase the $pK_a$ of carboxyl groups.

Mechanochemical coupling can be accomplished using the basic synthetic polypeptide system having the repeating sequence of elastin, $(L.Val^1-L.Pro^2-Gly^3-L.Val^4-Gly^5)_n$ where n was greater than about 50, and preferably greater than about 100, and cross-linking was achieved by $\gamma$-irradiation. To achieve a pH driven mechanochemical system, there can be incorporated randomly at position four occasional Glu residues such that the mechanochemical system was one in which there were four Glu residues per 100 residues of polypentapeptide. This can be referred to as $X^{20}$-4%Glu-PPP, the PPP for polypentapeptide and the $X^{20}$-to indicate cross-linking with a 20 Mrad $\gamma$-irradiation cross-linking dose.

The $X^{20}$-PPP alone will contract on raising the temperature by means of an extensively characterized inverse temperature transition, and when made more hydrophobic as in $X^{20}$-$(L.Ile^1-L.Pro^2-Gly^3-L.Val^4-Gly^5)_n$, the contraction occurs at lower temperature, and, when made less hydrophobic as in $X^{20}$-$(L.Val^1-L.Pro^2-Gly^3-Gly^4)_n$, the contraction occurs at a higher temperature. However, it is also now possible isothermically, to bring about a contraction by including a residue with a functional side chain that ma be made less polar (more hydrophobic) by a change in chemical potential, thereby lowering the temperature of the inverse temperature transition. Indeed $X^{20}$-4%Glu-PPP at 37° C. in phosphate buffered saline (0.15 N NaCl, 0.01 M phosphate) is relaxed at high pH where the more polar COO- is the dominant species and contracts on lowering the pH where the less polar COOH species is dominant. The temperature at which the inverse temperature transition occurs depends inversely on the average hydrophobocity of the polypeptide chain.

Chemical modulation of an inverse temperature transition constitutes a new mechanism of mechanochemical coupling. With the mechanism of charge-charge repulsion, polymethacrylic acid, when chemically cross-linked, is known to contract as the number of carboxylate anions is decreased by lowering the pH. In an analogous manner, $X^{20}$-4%Glu-PPP is extended when the side chains are ionized and contracts as the side chains are neutralized by lowering the pH. Of course, the charge density is an order of magnitude less for $X^{20}$-4%Glu-PPP near neutral pH such that the charge-charge interaction energy is expected to be small. Per unit mass of polymer there are 24 times as many carboxylic acid moieties in polymethacrylic acid as in 4%Glu-PPP.

Figure 9:
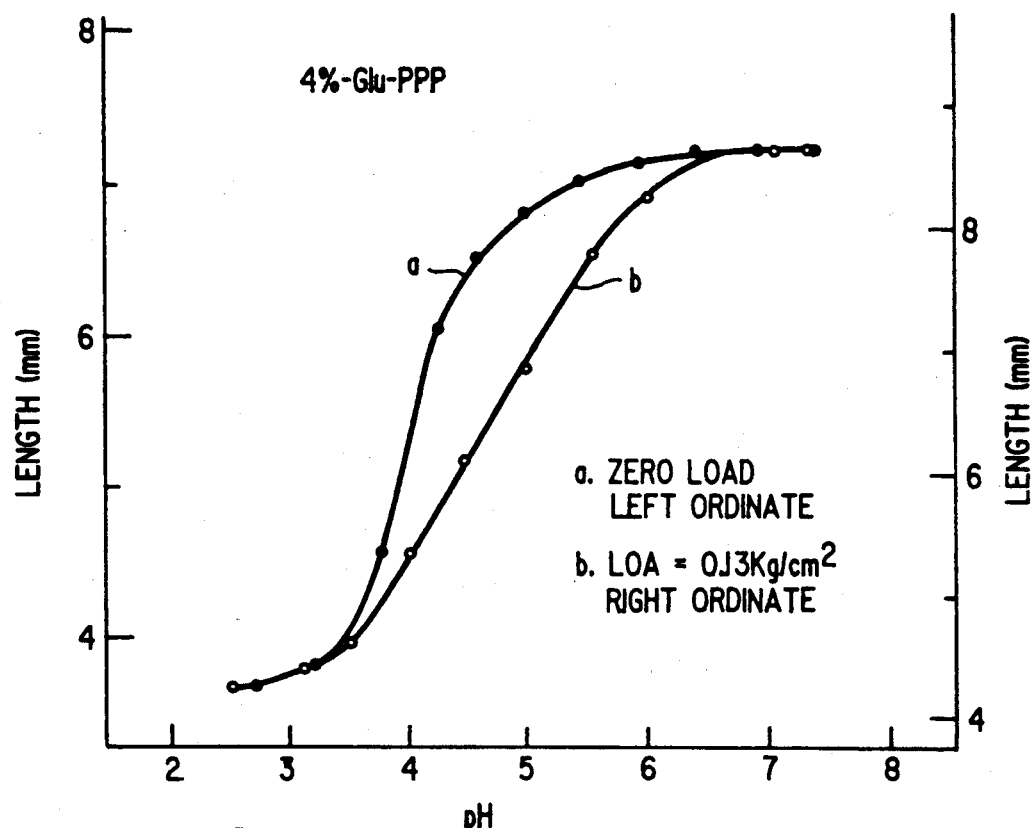

In the charge-charge mechanism, on stretching the mean distance between charges increases, this would relieve charge-charge repulsion; and more carboxyl side chains would be expected to ionize thereby releasing protons to the medium. Indeed, this has been observed for the polymethacrylic acid system; on stretching the elastomeric matrix was found to release protons. The release of protons from the polymethacrylic acid system on stretching is equivalent to the mathematical statement $(\partial \mu_i/\partial f)_{n_i} > 0$ where $\mu_i$ and f are the chemical potential for protons and the force, respectively, and the partial differential is at a degree of ionization, $n_i$. However, for $X^{20}$-4%Glu-PPP exactly the inverse is the case. As shown in FIG. 9, on stretching, the $pK_a$ of the carboxyl function increases indicating that, even though the mean distance between charges increases, the carboxylate anion becomes destablizied, that is, the free energy of the carboxylate anion increases on extension of an elastomer in which modulation of an inverse temperature transition is the dominant mechanism of mechanochemical coupling. Stated in terms of the critical partial differential, $(\partial \mu_i/\partial f)_n > 0$. This is demonstrated by the following illustrative and non-limitative Example.

EXAMPLE

Two titration curves of elastomer length as a function of pH for two different loads are measured. One curve is at zero load (zero force) and a second is at a load of 3.3 grams (i.e., $f = 3.2 \times 10^3$ dynes). In the case of the second curve, mechanical work is performed on lowering the pH. The weight is lifted through the distance of the contraction. From the midpoint of each titration curve, the $pK_a$ can be determined. Significantly on increasing the load the $pK_a$ increases. Each of these titration curves are stated as $(\partial l/\partial n_i)_f$, and, by carrying out the titrations at different loads, the curves provide information on $(\partial \mu_i/\partial f)_{n_i}$. Recognizing that, at the $pK_a$, the concentration of the carboxyl groups, [COOH], is exactly equal to the concentration of the carboxylate anions, [COO$^-$], this means that taking the $pK_a$ values as reference points is equivalent to comparison at constant $n_i$. On going from zero load to significant load of is positive. $\Delta \mu_i$ is determined as follows. Since $\mu = RT \ln[H^+]$ and $pH = -\log[H^+]$, then $\mu_i = 2.3$ RT $pK_a$. Therefore, for zero load, the chemical potential at which [COOH] = [COO-] is $\mu_i = -5.54$ kcal/mole, and, when loaded, the chemical potential at which [COOH] = [COO-] is $-6.37$ kcal/mole such that $\Delta \mu_i = -0.83$ kcal/mole. Therefore, $(\partial \mu_i/\partial f)_{n_i} 0 <$ and specifically for this exemplary mechanochemical system $(\partial \mu_i/\partial f)_n = -1 \times 10^7$ cm/mole.

Accordingly, when the mechanism of mechanochemical coupling is dominated by charge-charge interaction, $(\partial \mu_i/\partial f)_n$ is positive, whereas, when the mechanism is the chemical modulation of an inverse temperature transition, $(\partial \mu_i/\partial f)_{n_i}$ is negative. Whereas the former may be referred to a charge-charge repulsion mechanism, the latter may be analogously called the aqueous apolar-polar repulsion mechanism.

For $X^{20}$-4%Glu-PPP the same experiments can be carried out at constant force as described, i.e., $(\partial l/\partial n_i)_f$ or they may be carried out at constant length, $(\partial f/\partial n_i)_l$, where very large forces can be generated, e.g., forces equivalent to more than 1000 times the dry mass of the protein. Whether the chemical process is substrate binding, the binding of an allosteric effector, the change in the oxidative state of a cofactor such as the pyridine nucleotide, or phosphorylation/dephosphorylation, etc., the functioning of the protein appears to involve the chemical modulation of an inverse temperature transition. The diagnostic tool presented here for functional group ionization provides one example of how this new mechanism may be used advantageously.

Thus, in descriptive terms, when the elastic fiber is stretched, the hydrophobic contacts, which resulted from the inverse temperature transition, are now disrupted; the hydrophobic side chains become exposed to water, which organizes around the hydrophobic groups as clathrate-like water. The result is an increase in the free energy of the ionic species reflecting an apolar-polar repulsion energy. This is demonstrated with the following illustrative and non-limiting example.

EXAMPLE

When the basic (PPP) polypentapeptide is made more hydrophobic (as when Val$^1$ is replaced by Ile$^1$ to give Ile$^1$-PPP), and when Glu is similarly introduced and the sample is γ-irradiation cross-linked to give $X^{20}$-4%Glu-Ile$^1$-PPP, the $pK_a$ of the Glu side chain for a comparable load is increased by approximately one pH unit. Thus when the polypeptide is made more hydrophobic, the charged species is energetically less favorable, i.e., there is in water an effective apolar-polar repulsion energy. When, by contrast, $X^{20}$-PPP is without modification, it is found that raising the salt concentration of the medium lowers the temperature of the inverse temperature transition which means that, under isothermal conditions, raising the salt concentration causes contraction and lowering the salt concentration causes relaxation again reflecting an apolar-polar repulsion energy.

Since a change in hydrophobicity can change the temperature of the inverse temperature transition, a change in hydrophobicity at fixed temperature can bring about a contraction of the elastomer. In these terms a carboxyl group can be considered to be more hydrophobic than the carboxylate anion and by this mechanism a change in pH can be used to bring about contraction or relaxation. This will now be illustrated in the following example which is only intended to illustrate and not limit the present invention.

Figure 10A:
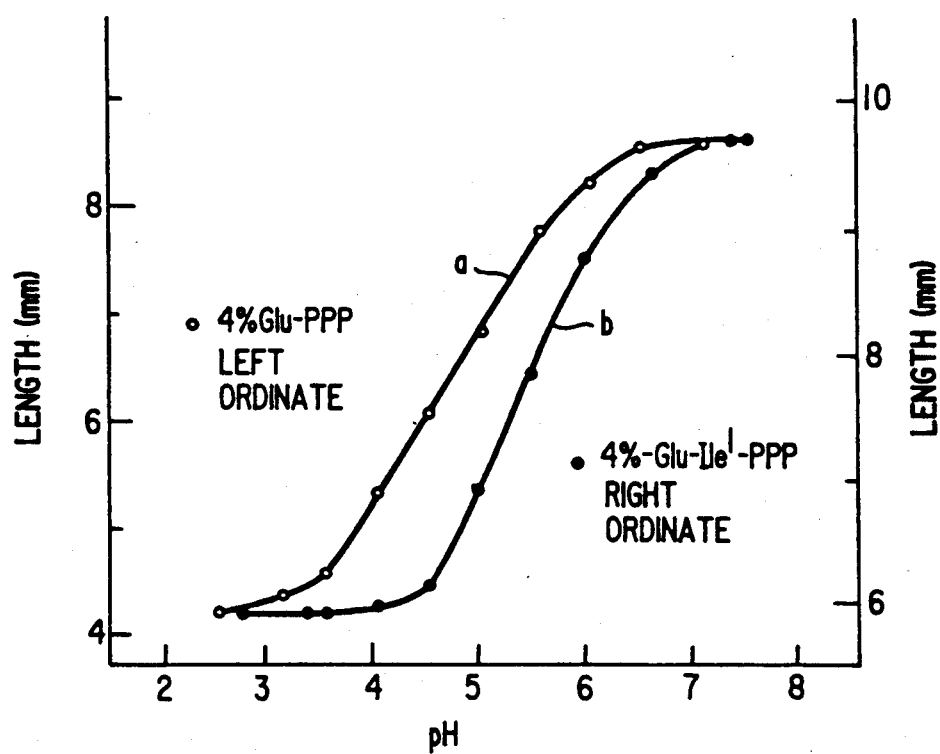
Figure 10B:
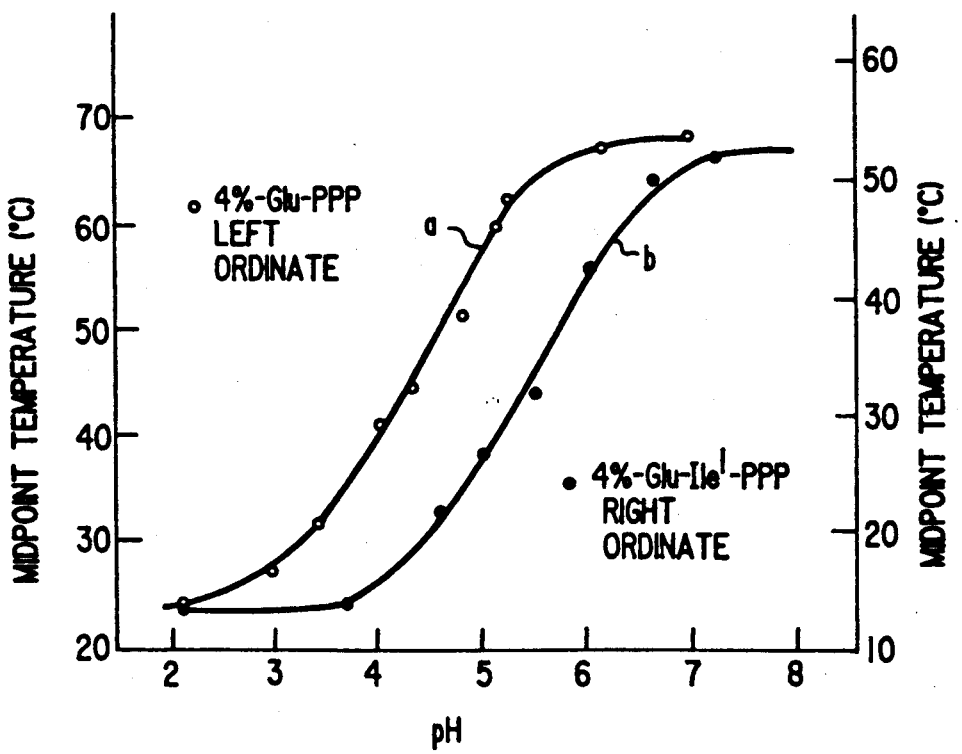

EXAMPLE

γ-irradiation cross-linked 4%-Glu-PPP, also referred to as 20%-Glu$^4$-PPP which is poly[(VPGVG):(VPGEG); 4:1]. As shown in FIG. 10a curve a, on lowering the pH from 7 to 3 in phosphate buffered saline (0.15 N Nacl, 0.01 M phosphate), the sample contracts from a length of 8.7 mm to 4.2 mm. The midpoint of this pH dependence of length curve at a constant load of approximately 1 gm/mm$^2$ defines a pK of 4.6 for the cross-linked 4%-Glu-PPP. When the same study is carried out with 4%-Glu-Ile$^1$-PPP, which is poly[(IPGVG):(IPGEG)] also at a ratio of 4:1, the midpoint of the pH dependence of length curve at a constant load of approximately 1 gm/mm$^2$ defines a pK of 5.4. When the temperature dependence of aggregation (coacervation) is monitored by turbidity development as a function of temperature at different values of pH, which is roughly analogous to following the process under zero load, the pK for 4%-Glu-PPP is 4.4 and that for 4%-Glu-Ile$^1$-PPP is 5.4. This is shown in FIG. 10b. What is apparent is that the pK of the Glu in Ile$^1$-PPP is shifted approximately 1 pH unit higher than that of the Glu in PPP. The pK shift is due to the hydrophobic effect as described above.

The above-described ionizable sequential polypeptides represent the first synthetic polypeptides or model proteins to exhibit mechanochemical coupling. As shown in FIG. 10a, a decrease in pH brings about a contraction in which a weight, 3.3 grams for cross-linked 4%-Glu-PPP and 2.2 grams for cross-linked 4%-Glu-Ile$^1$-PPP, is lifted through the distance of the shortening, that is, mechanical work has been achieved by a change in chemical potential. In doing so, these sequential polypeptides demonstrate a above-described new mechanism wherein contraction and relaxation are achieved by chemical modulation of an inverse temperature transition.

However, in addition to the ionizable sequential polypeptides described above, such as 4%-Glu-PPP, other suitable polypeptides may be used as described hereinbelow with an explanation therefor.

As noted in Ser. No. 062,557, the development of elastomeric force of elastin and elastin-like polytetra- and polypentapeptides is the result of an inverse temperature transition. Moreover, when the hydrophobicity of the peptide is changed, the temperature for association to form fibers changes and the temperature at which intramolecular order develops to produce the highly elastic state also changes. Notably, these changes occur in an entirely predictable manner, i.e., when the hydrophobicity is increased, the transitions occur at lower temperature, and when the hydrophobicity is decreased (making the polypeptide chain more polar, the transitions occur at higher temperature. In brief, this type of structural mechanism involves a transition from a higher to a lower entropy state for the polypeptide upon raising the temperature.

However, it was also discovered that a second type of mechanism can be used whereby a change in chemical potential can be used to shift the temperature for a regular transition on going from an inelastic lower entropy state to an elastic higher entropy state. A chemical process is used to lower the temperature of the transition to turn "on" the elastomeric force. For example, the inelastic α-helix which is in an extended state is converted to the highly elastic spiral state, which then can be used to lift a load. In essence, any chemical process which raises the free energy of the α-helix and/or lowers the free energy of the spiral state can be used to cause the elastic contraction. A discussion of the various approaches to effect changes in chemical potential follows hereinbelow.

First, it is possible to utilize a change in pH as the chemical process for effecting mechanochemical coupling. As a practical matter, any amino acid residues can be used in the PTP and PPP systems with this mechanism as long as the residues respond to changing pH by a change in degree of ionization without unduly affecting the β-spiral structure, i.e., without unduly disrupting intrapentamer and intratetramer hydrophobic interactions and interrepeating unit hydrophobic interactions.

For example, in the PPP system having the generic formula:

$$-\text{VPGVG}-_n$$

by making appropriate substitutions of polar amino acid residues, the inverse temperature transition can be shifted from about 25° C. to a higher temperature. If the substituted amino acid residue also has an ionizable side chain, i.e., R group, the onset of the transition will be shifted to an even higher temperature. Thus, the elastomeric force development of such a system can be effectively turned "on" or "off" by appropriately changing the pH.

In general, by making the repeating unit of a particular elastomer more polar, i.e., less hydrophobic, the temperature transition is shifted to higher temperature. Consistent with this principle, it has been found advantageous to substitute, to a variable extent, certain residues of the PPP and PTP systems with a more polar amino acid residue such as Glu, Asp, His, Lys or Tyr, for example.

Figure 11:
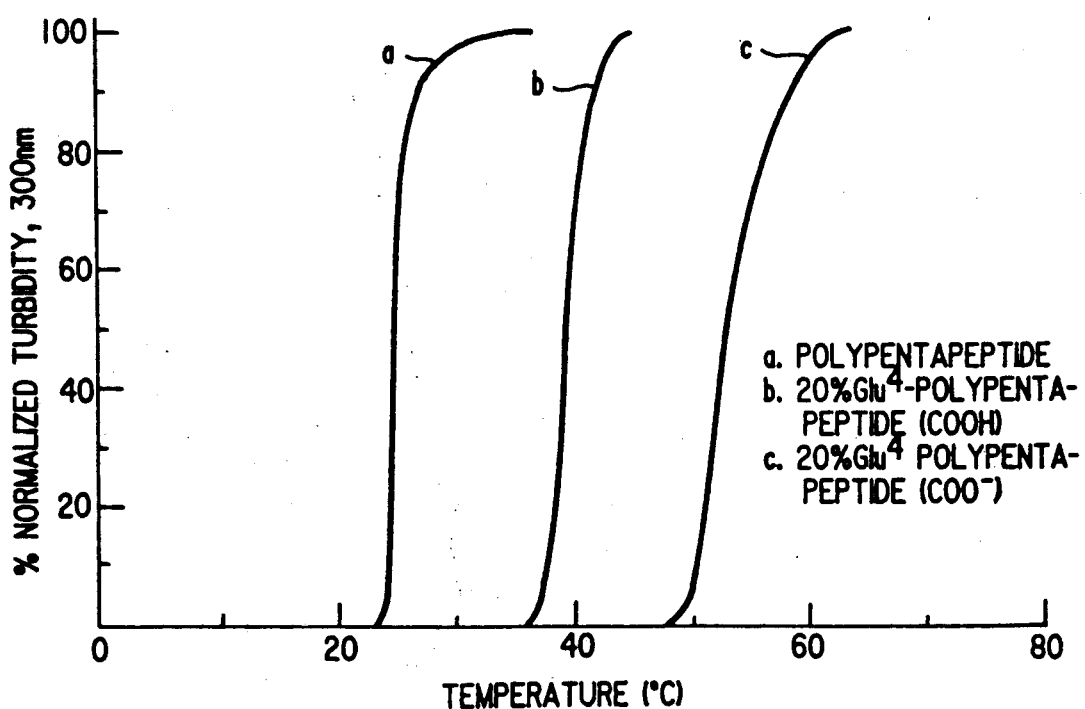

For example, as shown in FIG. 11, the inverse temperature transition can be followed by means of the temperature profiles for aggregation for the polypentapeptide and its 20% Glu$^4$ analog. Changing one in five Val$^4$ residues to a Glu$^4$ residue, when the pH is 2 where the side chain is the carboxyl, changes the onset of the inverse temperature transition from 25° C. to 37° C. On ionization of the side chain to form the carboxylate anion at pH 6, the onset of the inverse temperature shifts further to 70° C. or greater. Once the 20% Glu$^4$-polypentapeptide is cross-linked to form the elastomeric matrix, the elastomer can most effectively at 50° C. be turned "on" at pH 2 and "off" by changing the pH to 7. Thus, a chemomechanical transducer is afforded. If 50° C. is not the desired temperature, for example, if lower temperature is desired instead, then more hydrophobic residues could be used in place of Val$^1$ and Val$^4$. Or the medium could be changed from water to phosphate buffered saline (PBS) where 37° C. becomes the workable temperature. For water, for example, with Ile$^1$-polypentapeptide which has a transition midpoint of about 10° C., the inclusion of a more polar residue, such as Glu, Asp, His, Lys, or Tyr, for example, in every third pentamer at position four raises the temperature of the transition toward 30° C. for the non-ionized state. However, in accordance with the above, certain residues may be replaced with the more polar residues more or less frequently than in every third pentamer. For example, the substitution of either or both of Val$^1$ and Val$^4$ can be made in every PPP pentamer or in only 1 of 5, 1 of 10 or 1 of 20, or even 1 of 100 pentamers. However, generally, enough of a substitution will be made to effect some shift in temperature transition without effecting the formation of the β-spiral structure.

In particular, in accordance with this mechanism of altering chemical potential, in the PPP and PTP systems any amino acid peptide-forming residues may be used in place of the native residues as long as the substituted residues are ionizable and do not effect the structural development of the polypeptide sequence which is necessary for the development of elastomeric force.

However, for the PPP system, i.e., $-\text{VPGVG}-_n$, it is preferred that position 1, conveniently designated α be either a peptide-forming residue of L-valine or a peptide-forming residue of L-Glu,L-Asp,L-His,L-Lys and L-Tyr and Other ionizable peptide-forming L-amino acid residues.

It is also preferred that position 4, conveniently designated Ω, have the same substitution pattern as described above for α.

Notably, although all amino acid residues are of the L-form in the present application unless otherwise specified, the above L-designations are used for clarity.

However, for position 3, designated as ρ, it is preferred that the same either be glycine or a peptide-forming residue of D-Glu, D-Asp, D-His, D-Lys and D-Tyr and other ionizable peptide-forming residues of D-amino acid residues.

In particular, in accordance with the present invention it has been found that the use of L-amino acid residues at position 3 of the PPP system, gives rise to a hard plastic phase when the temperature of the system is raised above the transition temperature. Hence, peptide-forming ionizable amino acid residues of the D-form are used as substitutes at position 3 for glycine.

The term "other ionizable peptide-forming amino acid residues" of either the D- or L-form refers to all naturally occurring or synthetic amino acids which contain ionizable R groups in the side chain thereof. For example, instead of using Glu containing a R group of ($-CH_2-CH_2-CO_2H$), a homologue of Glu can be used having a R group of ($-CH_2-CH_2-CH_2-CO_2H$). Alternatively, synthetic amino acids may be used having more than one ionizable function in the R group thereof such as $'CH-(CO_2H) CH_2 CO_2H$) or $-CH_2(CO_2H)-CH-CO_2H$). In any event, in view of the above disclosure, a wide variety of such other peptide-forming amino acid residues will be apparent to one skilled in the art.

Thus, for the PPP system, bioelastomers are contemplated which contain repeating units containing elastomeric tetrapeptide or pentapeptide units or a mixture thereof, wherein the repeating units contain amino acid residues selected from the group consisting of hydrophobic amino acid residues and glycine residues, wherein the repeating units exist in a β-turn which contains a polypentapeptide unit of the formula:

$$-\alpha P \rho \Omega G-$$

wherein

P is a peptide-forming residue of L-proline;

G is a peptide-forming residue of glycine;

α is a peptide-forming residue of L-valine or a peptide-forming residue of L-Glu, L-Asp, L-His, L-Lys and L-Tyr and other ionizable peptide-forming L-amino acid residues thereof;

ρ is a peptide-forming residue of glycine peptide-forming residue of D-Glu, D-Asp, D-His, D-Lys and D-Tyr and other ionizable peptide-forming D-amino acid residues thereof; and Ω is a peptide-forming residue of L-valine or a peptide-forming residue of L-Glu, L-Asp, L-His, L-Lys and L-Tyr and other ionizable peptide-forming L-amino acid residues thereof; and wherein n is an integer of from 1 to 5,000; with the proviso that in at least one repeating pentapeptide unit of the bioelastomer, at least one of said α or Ω is a peptide-forming residue selected from the group consisting of residues of L-Glu, L-Asp, L-His, L-Lys and L-Tyr and other L-residues as specified, or said ρ is a peptide-forming residue selected from the group consisting of D-Glu, D-Asp, D-His, D-Lys and D-Tyr and other D-residues as specified.

For the PTP system, having the formula $-VPGG-_n$, it is preferred that position 3, designated as φ, be either a peptide-forming residue of glycine or a peptide-forming residue of D-Glu, D-Asp, D-His, D-Lys and D-Tyr and other ionizable peptide-forming D-amino acid residues thereof.

It is preferred that position 4 of the above system, designated as δ, be either a peptide-forming residue of glycine or a peptide-forming residue of L-Glu, L-Asp, L-His, L-Lys and L-Tyr and other ionizable peptide-forming L-amino acid residues thereof.

Of course, the term "other ionizable peptide-forming amino acid residues" of either the D-or L-form have the definition set forth above.

Thus, for the PTP system, bioelastomers are contemplated which contain repeating units containing elastomeric tetrapeptide or pentapeptide units or a mixture thereof, wherein the repeating units contain amino acid residues selected from the group consisting of hydrophobic amino acid residues and glycine residues, wherein the repeating units exist in a β-turn which contains a polytetrapeptide unit of the formula:

$$-VP\phi\delta-_n$$

wherein

V is a peptide-forming residue of L-valine;

P is a peptide-forming residue of L-proline;

φ is a peptide-forming residue of D-Glu, D-Asp, D-His, D-Lys and D-Tyr and other ionizable peptide-forming D-amino acid residues thereof; and δ is a peptide forming residue of L-Glu, L-Asp, L-His, L-Lys and L-Tyr and other ionizable peptide-forming L-amino acid residues thereof; and wherein n is an integer of from 1 to 5,000; with the proviso that in at least one repeating polytetrapeptide unit of the bioelastomer, at least one of said φ or δ is a peptide-forming amino acid residue selected from the groups consisting of D-Glu, D-Asp, D-His, D-Lys and D-Tyr and other ionizable peptide-forming D-amino acid residues thereof; or L-Glu, L-Asp, L-His, L-Lys and L-Tyr and other ionizable peptide-forming L-amino acid residues thereof, respectively.

Specifically, it is noted that the above substituted tetrameric and pentameric units may be incorporated together into a bioelastomeric polypeptide in accordance with the present invention.

For example, in the PPP system, the appropriate mix of Ile[1] and Val[1] and of Val[4] and the more polar side chain at position four allows the midpoint of the transition to be selected over a temperature of 10° C. to above 30° C. On ionization the transition shifts to a higher temperature yet. For example, if the non-ionized analog exhibited a transition midpoint near 30° C. and that the β-spiral structure were formed and the development of elastomeric force were essentially complete by 37° C., then on ionization (e.g., on raising the pH above the pK of the ionizable function) the transition midpoint would shift to a higher temperature; the structure would unwind and the elastomeric force will be turned off. Lowering the pH to below the pK causes the elastomeric force to turn back on. Thus, a change in the activity of the hydrogen ion becomes the switch.

In order to further illustrate the above aspect of the present invention, an example is provided only for the purpose of illustration and is not intended to limit the present invention.

EXAMPLE

Instead of using the basic PPP system, $-VPGV-G-_n$, Ile[1]-PPP, i.e., $-IPGVG-_n$ is employed. For this system, elastomeric force is observed to develop between 5° C. and 25° C. However, the polypeptide elastomer is then made more polar by the incorporation therein of Glu[4] in approximately every third pentamer. This results in a shift of the temperature transition to some 20° C. higher in temperature such that comparable elastomeric force does not develop until 45° C.

However, since a change in the pH of from 2 to 7 at 37° C. effectively causes a change from one curve to another, i.e., the ionized to non-ionized state, elastomeric force is turned "on" or "off" thereby. This switching function is due to a change in chemical potential.

Notably, just as changing the temperature from 20° C. to 40° C. causes an elastic contraction to lift a load, it is now possible to accomplish the same result by changing the pH from 2 to 7 and back again.

Thus, it is possible to controllably turn "on" and "off" elastomeric force to perform work. Moreover, as the development of entropic elastomeric force appears to be responsible for this capability, this capability is, perhaps, best described as entropic motive force (EMF).

Thus, it can be seen that although using 20% Glu$^4$-PPP it is possible, with this system, to turn "on" elastomeric force at pH 2 and to turn "off" the same at pH 7, at pH values near the pK$_a$ of glutamic acid, i.e., 4.25, elastomeric force development of the bioelastomer is very sensitive to small incremental changes in pH. Hence, a sensitive pH meter can be designed using the above principle.

Of course, the pH dependency of the elastomeric force development of the bioelastomer will depend upon which polar, ionizable R groups are present and the pKa values of these groups. For example, the pKa of the R group ($-CH_2CH_2CO_2H$) of glutamic acid is about 4.2, while the respective value for aspartic acid ($-CH_2CO_2H$) is about 3.9, and the same for histidine is 7.0. In any event, these values are clearly well known and can be used to design bioelastomers in accordance with the above principles which afford variable sensitivity to changes in pH as measured by the change in elastomeric force.

Although the chemical potential of the present bioelastomers can be most easily affected by a change of pH, there are at least three other approaches to accomplishing the same end.

First, it is also possible to change the chemical potential of the bioelastomer by exposing the bioelastomer to a changing concentration of $Ca^{+2}$. Generally, concentrations in the range of about $10^{-1}$ to $10^{-7}$M may be used depending on the binding constant. As such, the bioelastomers of the present invention, like many polypeptides and proteins, can bind to $Ca^{+2}$ ions with binding constants as high as $10^6$/M or greater. Of course, with this approach it is necessary to incorporate amino acid residues offering $Ca^{+2}$ binding sites, such as Glu and the dicarboxylate analog thereof.

Secondly, it is also possible to change the chemical potential of the bioelastomer by a reversible phosphorylation-dephosphorylation cycle. In particular, it has been found that just as ionization changes the hydrophobicity of the elastomeric polypeptide, and thus changes the temperature of an inverse temperature transition, phosphorylation of the polypeptide will, in effect, turn "off" elastomeric force—making the polypeptide more polar—and dephosphorylation of the polypeptide will, in effect, turn "on" the elastomeric force.

More specifically, by using various kinase and phosphatase enzymes well-known to those skilled in the art, it is possible to effect phosphorylation-dephosphorylation of PPP systems which incorporate hydroxyl-containing amino acids in the elastomeric repeating units, such as Ser, Thr and Tyr or even Hyp.

In more detail, when using phosphorylation-dephosphorylation cycle, instead of using the polar, ionizable peptide-forming residues as described above for the PTP and PPP systems, in essence polar hydroxyl-group-containing peptide-forming amino acid residues are used instead. Specifically, residues of Ser, Thr and Tyr or Hyp may be used bearing in mind the use of the D-form at either position 3 of the PTP system or the PPP system and the use of the L-form at either position 4 of the PTP position or positions 1 and/or 4 of the PPP system.

Of course, other hydroxyl group-containing peptide-forming amino acid residues may also be used with the above restrictions in mind for the D- and L-forms. Any naturally occurring or synthetic hydroxyl group-containing peptide-forming amino acid residues may be used. For example, instead of using Ser containing a R group of $-CH_2OH$), a homologue of Ser may be used having a R group of $CH_2 CH_2 OH$). Or, instead of using Thr containing a R group of ($CH_3-CH(OH)-$, a homologue of Thr may be used having a R group of ($CH_3-CH(OH)-CH_2-$.

Alternatively, synthetic amino acids may also be used having more than one hydroxyl group per residue. In any event, in view of the above disclosure, a wide variety of other such peptide-forming amino acid residues would be apparent to one skilled in the art.

As noted above, various enzymes may be used to effect phosphorylation-dephosphorylation, such as protein kinase c and cyclic AMP dependent kinase. These enzymes and their use, in general, for phosphorylation-dephosphorylation are known to those skilled in the art. See *Int. J. Biochem.*, 18 (6), 497–504 (1986). The particular substrate for use in the present invention will depend on the transition desired. The operable concentrations of each can be ascertained by those skilled in the art in view of the above disclosure and on a case by case basis.

Notably, when using protein kinase C, it is desirable to incorporate a Lys or Arg residue following the site to be phosphorylated-dephosphorylated. Typically, spacers of 1 or 2 amino acid residues are used there between. When using cyclic AMP dependent kinase, it is desirable to incorporate a Lys or Arg residue preceding the site to be phosphorylated-dephosphorylation.

Thirdly, it is also possible to effect the switching mechanism by using an amidation-deamidation cycle, whereby glutamine and/or asparagine residues in the elastomeric repeating unit are deamidated to, in effect, produce, at pH 7, an anionic carboxylate side chain. This is specifically contemplated as being equivalent to the deprotonation of a carboxylic acid side chain group for purposes of the present invention. In accordance with this equivalent embodiment, upon deamidation, the inverse transition temperature would increase to, in effect, turn "off" elastomeric force, whereas the amidation of a carboxylate side chain would be used to turn "on" elastomeric force.

Thus, all of the above alternatives 1) protonation-deprotonation, 2) metallation-de-metallation with $Ca^{+2}$ ion, 3) phosphorylation-dephosphorylation, and 4) amidation-deamidation cycles can all be used to effectively turn "on" and "off" elastomeric force development in accordance with the present invention.

These elastomeric strips are mechanochemical engines that can be driven by chemical concentration gradients and as emphasized here when run in reverse by putting in the mechanical energy by stretching are capable of doing chemical work, for example, transferring protons or other suitable chemical agents against a concentration gradient.

B. Engines for the Conversion of Chemical Work to Mechanical Work

The elastomeric materials can also be used in a reversible mechanochemical engine of the Katchalsky design instead of conventionally used collagen and rubber.

The mechanochemical engine of Katchalsky utilized a rotary motion making use of a belt of collagen that was made to contract on introduction into a medium of high salt concentration. The effect of the high salt concentration was to lower the transition temperature for thermal denaturation. Due to the relatively high heats of denaturation involved, the concentration gradients that were required were very large. For example, the two baths that were used were 11.25 N LiBr and O or 0.3 M LiBr. However, with the present bioelastomers, small heats of coacervation are involved, ~1 cal/gram, whereby relatively small concentration gradients are effective in bringing about contractions as shown in FIGS. 5 and 6 where the concentrations were 0.15 N and pure water. Quite significantly, sodium chloride is an effective salt. Thus, using the engines of the present invention, one can drive the shaft in reverse and thereby achieve desalination, i.e., to transfer salt up a concentration gradient. This will now be explained.

The physical basis for such a desalination may be described as follows. When $X^{20}$-PPP is stretched, hydrophobic groups become exposed; and the elastomer takes up water in an exothermic reaction as the exposed hydrophobic groups become surrounded with clathrate-like water. This is analogous to the swelling that occurs on lowering the temperature from 40° to 20° C. where there is a 10 fold increase in volume for $X^{20}$-PPP. The more hydrophobicity expressed by a polypeptide, the less favorable is the situation for ions. This is demonstrated by the raised $PK_a$ of the Glu side-chain for the more hydrophobic $X^{20}$-4%-Glu-Ile$^{Ile1}$-PPP and by the raised pKa on stretching $X^{20}$-4%-Glu-PPP. In both of these cases the increased expression of hydrophobicity results in the free energy for formation of the carboxylate anion being less favorable. Therefore stretching $X^{20}$-PPP in a high salt solution results in the uptake of solution into the elastomer which is low in ions; the excess solution which is drained off while $X^{20}$-PPP is stretched, is at a higher salt concentration. When the fiber is relaxed it gives off a solution which is at a lower salt concentration. By appropriately repeating this process with directed solution flows, the result would be splitting of a salt solution into two solutions one higher and the other lower in salt concentration.

For a belt comprised of the present elastomeric polypeptides in which the mechanism of contraction involves the aqueous apolar-polar repulsion which gives rise to a modulable inverse temperature transition, however, there are many more processes that can be used to drive the engine. Any reversible chemical process that would make chemical moieties attached to the polypeptide chain either more or less polar could be used to drive a thermomechanical engine or when driven externally in reverse could be used in a preparative manner (i.e., to prepare the chemical species which caused contraction). For example, the chemical to be prepared can be the reduced species of a redox couple or, as in the pH driven mechanochemical engine, the couple is protonation/deprotonation or the couple can be phosphorylation/dephosphorylation. Driving the system in reverse by stretching results in the pumping of protons or, in effect, electrons against their concentration or electrical potential gradients.

In general when contraction is achieved in a reversible manner, as it can be in the chemical modulation of the inverse temperature transition of the present elastomeric polypeptides, then stretching becomes the free energy input with which to reverse the chemical process. The reversed chemical process can be a means whereby a chemical moiety attached to the elastomeric polypeptide is made less polar (relatively more hydrophobic) or whereby the free energy of the clathrate-like water is increased.

The present invention affords, in part, mechanochemical engines which are capable of interconverting mechanical and chemical work.

Figure 8A:
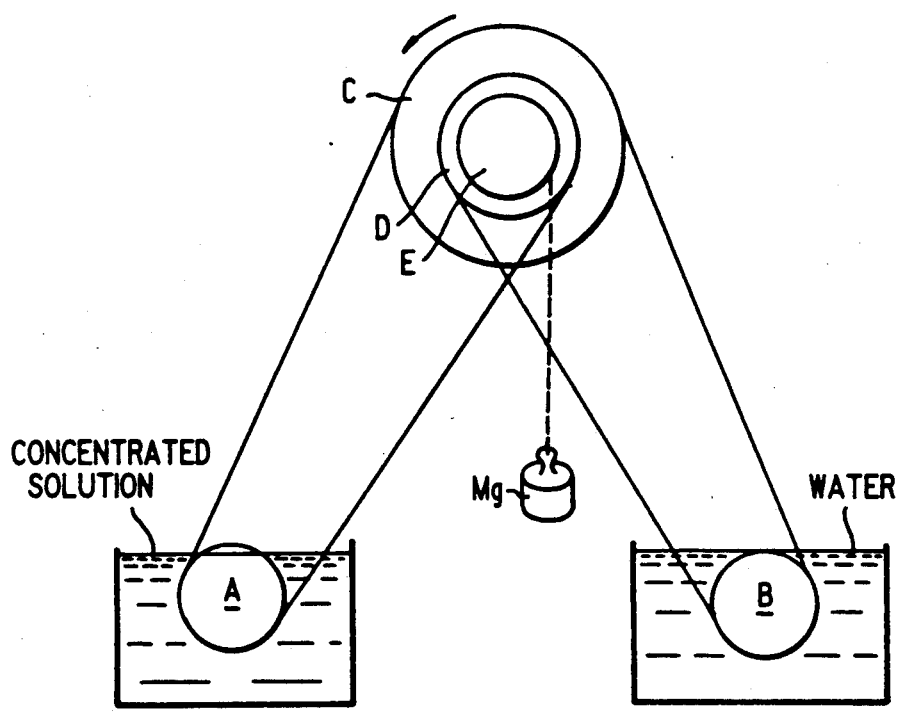

In perhaps the simplest construction, in essence using the Katchalsky design but with the elastomers of the present invention instead of collagen, shown in FIG. 8a as described by Katchalsky, a closed loop of the cross-linked elastomeric material of the present invention is wound around the pulleys as shown. The following description is obtained from Katchalsky and co-workers, see *Nature*, supra, modified and introduced here solely to elucidate the use of the present elastomers in mechanochemical engines. When first pulley A is dipped into a sodium chloride or other salt solution having a concentration of as low as 0.15 N, using a phosphate buffered saline, the elastomeric material contracts and exerts equal forces on the rims of concentric pulleys C and D, which are rigidly connected. While concentrations of salt solution of as low as 0.15 N in the "concentrated" bath may be used, it is, however, preferred to use more concentrated solutions such as in the range of from 1 N to saturated salt solutions. For example, 11 N solutions may be used, as with LiBr. Since the radius of C is larger than that of D, a net rotary moment will act on the compound-pulley C-D and will cause a counter-clockwise rotation. The rotation will bring a new part of the elastomeric belt into the salt solution which reproduces the same effect. At each revolution of pulley C-D, a longer stretch of fiber is brought in by pulley C then is taken out by pulley D. For a steady-state operation of the engine the net length of elastomeric strip introduced by C-D into the salt solution should be counterbalanced by the contraction due to the chemical interaction of elastomeric strip with salt. The reverse process occurs at second pulley B, which dips into water which washes out the sodium chloride and relaxes the elastomeric strip.

Mechanical work may be obtained by, for example, attaching a suitable weight to the end of a cotton thread wound in the proper direction through pulley E, which has a common axis with C-D. While the engine is working, salt is transferred from the concentrated solution to the dilute one.

Figure 8B:
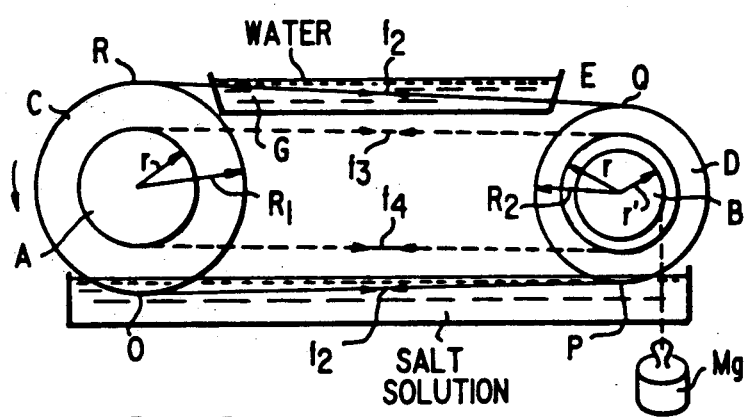

A modification of the FIG. 8a design is shown in FIG. 8b. In FIG. 8b, a closed loop of elastomeric material, preferably a strip, E, passes through a sodium chloride solution in the lower bath F and through water in upper bath G. The transmission disks, A and B, rigidly coupled with the main wheels C and D, respectively, are connected by a loop of an inelastic string, such as a cotton or synthetic fiber. As the lower bath is filled with sodium chloride solution, a contractile force develops in the portion of the elastomeric strip which is immersed in the solution. This force acts on wheels C and D and tends to rotate the former counter-clockwise and the latter in a clockwise direction. The system of wheels will rotate in the direction of the algebraic sum of the moments acting on C and D.

For example, if transmission disks A and B are of equal radius, and if wheel C has a larger radius than that of D, the wheels in the salt bath will turn counter-clockwise. Thus, do the ratios of the various pulleys and the extent of elastomeric concentration influence the operation of the machine.

Figure 8C:
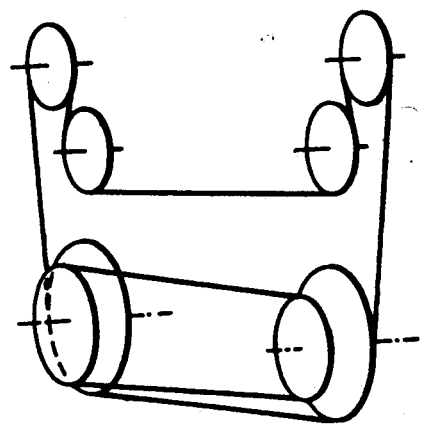

A further modification is shown in FIG. 8c, wherein the upper two pairs of wheels are added to facilitate the entrance of the elastomeric strip into the water bath.

In the construction of the above machines, the pulleys and wheels may be made of glass, plastic, wood or even metal.

Generally, the salt solution for the concentrated bath has a salt concentration in the range of 0.1 to about 11 N or as high as can be obtained with saturation of the solution. However, it is preferred that concentrations of about 0.1 to 5 N be used.

Although sodium chloride is the preferred salt for use due to the fact that it is inexpensive and readily available, any salt may be used which functions similarly. Examples of such salts are the alkali and alkaline earth metal halides. Other salts are the alkali and alkaline earth metal nitrates, carbonates, cyanates, thiocyanates and sulfates. In addition to the alkali and alkaline earth metal salts described, any water-soluble salts of the alkali and alkaline earth metals or other metals may be used, such as the water-soluble transition metal salts and rare earth metal salts. However, one skilled in the art would ascertain which salts are water-soluble.

Additionally, it is noted that the machine described may be constructed with either small or large dimensions. Further, the mechanical power output is conveniently measured by means of a friction belt on an auxiliary wheel coupled to the machine.

C. Engines for Effecting Desalination of Sea Water and Brackish Water

The present invention also provides engines which are capable of effecting a solvent-based conversion of mechanical work to chemical work. This is, perhaps, best exemplified in an engine for effecting desalination of sea water and brackish water as described hereinbelow.

The sequential polypentapeptide of elastin (L.Val$^1$-L.Pro$^2$-Gly$^3$-L.Val$^4$-Gly$^5$)$_n$, when cross-linked by $\gamma$-irradiation and when in equilibrium with water undergoes a reversible contraction on raising the temperature from 20° to 40° C. This is the result of an inverse temperature transition. In accordance with this aspect of the invention, a change in salt concentration causes a shift in the temperature of the inverse temperature transition and in particular that contraction and relaxation can be achieved by such changes in ionic strength. This is the first demonstration that changes in chemical potential can produce contraction and relaxation in a neutral polymer and in particular in a synthetic polypeptide containing only aliphatic (Val and Pro) or no (Gly) side chains where the process is one of ionic strength modulation of an inverse temperature transition. This will now be demonstrated.

The polypentapeptide (PPP) was synthesized as previously described. This material is soluble in water in all proportions below 25° C. but on raising the temperature aggregation occurs. Aggregation may be monitored by following the temperature dependence of solution turbidity as shown above for water and for phosphate buffered saline (0.15 NaCl, 0.01 M phosphate) which is the physiological buffer system. The phosphate buffered saline (PBS) causes aggregation to begin at a lower temperature while the effect of pH is minimal. The aggregates settle to form a more dense phase called the coacervate which in water is 38% peptide and 62% water by weight at 40° C. The coacervate is viscoelastic phase which can be formed in any desired shape and then $\gamma$-irradiation cross-linked at 20 Mrad ($20\times10^6$ radiation absorbed dose) to form an elastomeric matrix. Within the limits of nuclear magnetic resonance detability for carbon-13 and nitrogen-15 enriched polypentapeptide, the coacervate is essentially indistinguishable from the cross-linked elastomeric matrix demonstrating that $\gamma$-irradiation results in no NMR-detectable breakdown of the polypentapeptide. Elastomeric bands so prepared are characterizable by stress/strain and thermoelasticity studies in a previously described apparatus. When the sample is equilibrated in solution at 37° C., stretched to 40% extension and the force is monitored as a function of temperature at the fixed extension, the thermoelasticity curves are obtained for water and for PBS where elastomeric force is seen to develop abruptly at temperatures which approximately correspond with the temperature profiles of turbidity formation. As the presence of PBS causes the development of elastomeric force to occur at lower temperature, it is now be possible to remain at a fixed intermediate temperature, for example at 25° C., and to achieve contraction and relaxation by changing between water and PBS solutions. This is shown in FIG. 6 for conditions of a fixed extension (28% extension at 25° C. in PBS) while monitoring force and in FIG. 10B for conditions of a fixed force (1.6 grams obtained at 20% extension in PBS at 25° C.). Thus the polypentapeptide of elastin is seen to exhibit mechanochemical coupling in response to changes in ionic strength of the medium. As also seen in FIG. 6, there is essentially complete reversibility of relaxation and contraction.

Modulation of an inverse temperature transition is achievable with smaller changes in chemical potential (less chemical work) which is consistent with the small endothermic heat of the inverse temperature transition, i.e., the heat of polypentapeptide coacervation is about 2 cal/gram. Accordingly, this provides a particularly favorable type of system for free energy transduction. Desalination is achieved by driving such a polypentapeptide-based mechanochemical engine backwards through the application of mechanical work.

The construction and operation of the desalination apparatus of the present invention will now be described by reference to FIG. 7. Desalination is used herein to indicate a decrease in salt concentration.

FIG. 7 illustrates a simple desalination apparatus which entails a container having a piston-like apparatus for the application of mechanical work to stretch the elastomeric material housed in the container. Preferably, the mechanical work is applied manually. The apparatus also has, in simple form, a $\gamma$-shaped spigot for allowing fill water, which may be sea water or brackish water, to charge the container or for allowing discharge of the same from the container.

The elastomeric material is made of the elastomeric materials of the present invention with the precise composition being selected depending upon the temperature conditions under which the desalination unit is to be operated. For example, a different composition would be required depending upon whether the desalination unit would be operated under arctic or tropical conditions.

The fill water is charged into the container while manually stretching the elastomer. After allowing the elastomer to equilibrate with fill water for a short period of time, generally from about 1 second to about 20 minutes, the excess fill water is allowed to drain. Then, the elastomer is manually allowed to relax, and desalinated water is released from the container. While some salts may remain in the desalinated water, their concentration will be below the physiological concentration of salt, rendering the water potable.

From FIG. 7, it is noted that three sequential steps are involved. In detail, the first step involves filling the chamber with salt water and stretching, either automatically or manually, the elastomer. This allows salt-diminished water to move into the hydrophobic elastic matrix. The piston can either be held in a stretched position manually or locked into position by a locking means at the top of the container. The stretched position is maintained for about 30 seconds to about 10 minutes.

Then, the concentrated salt water is drained off, which keeps the elastomeric matrix in a stretched position.

Finally, the elastomer is relaxed while draining off desalinated water for drinking.

The desalinated water may, in fact, contain some salt, however, it is sufficient if the water contains a lesser amount of salt than is physiologically present in the human body. Under this condition, the water is potable.

In this design, the elastomeric material in the housing is fastened to either end of the housing being free at the sides to stretch or relax. The elastomeric material may be fastened to either end with clamps, for example.

The elastomeric material may be present as a single matrix or as a number of strips packed into the housing with a sufficient density.

As a variation to the basic design in FIG. 7, it is, of course, also possible to link two or more containers containing the elastomeric matrix in sequence, whereby the fluid output of one unit becomes the fluid input of the second.

Figure 12B:
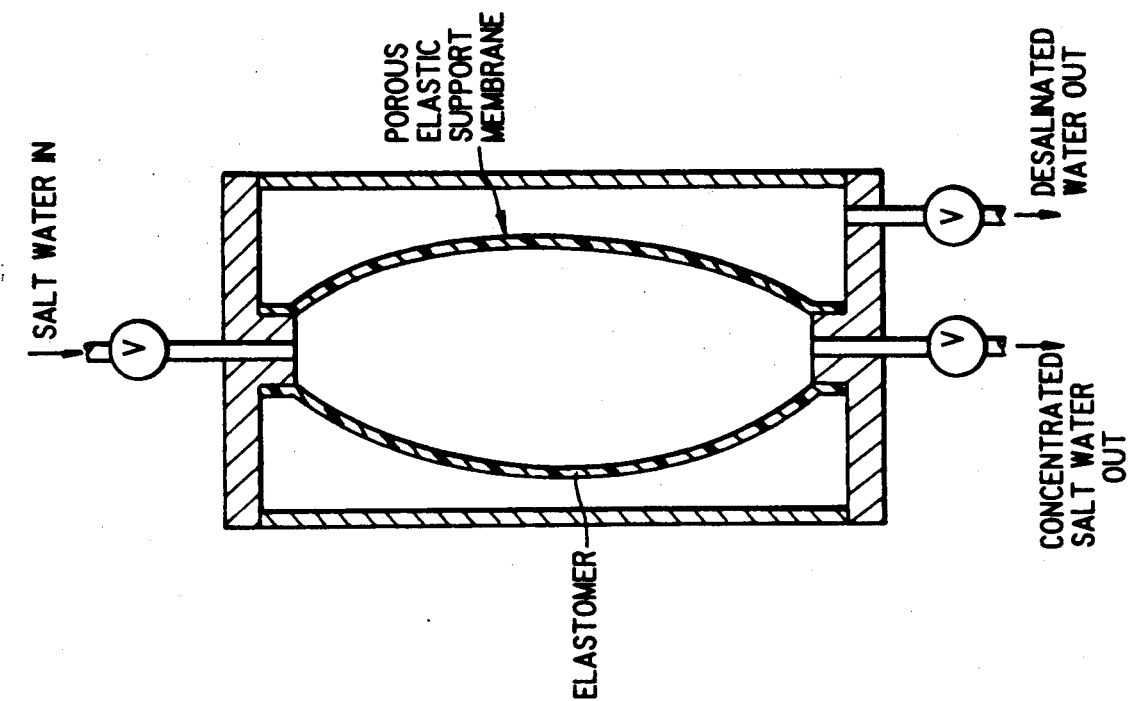
Figure 12A:
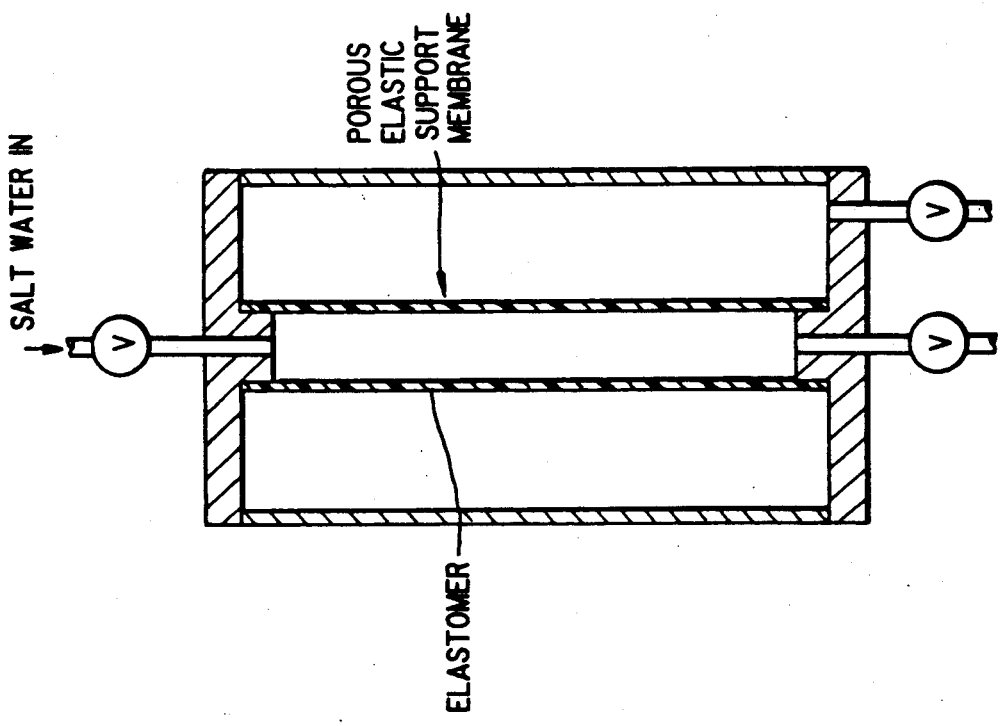

Additionally, a design in accordance with FIG. 12 is also possible whereby two concentric cylinders or tubes are involved, the center tube being made of the elastomer. In such a design, as shown, salt water is allowed to enter the central cylinder or tube and through the application of sufficient hydrostatic pressure desalinated water diffuses through the elastomeric matrix and porous elastic support membrane to the outer cylinder or tube. The application of pressure to the inner cylinder or tube accelerates diffusion of water.

The alternate desalination unit utilizing the same basic properties and process as just described operates by passing a salt solution under pressure through a tube containing cross-linked PPP or the appropriate analog. With the hydrostatic head desalinated water will pass through the walls of the elastic tube and the solution which exits through the lumen of the tube will be concentrated in salt. Transport through the wall effects desalination.

In essence, two solutions are produced having two different concentrations. This may be referred to as the formation of a concentration gradient or a chemical separation. Chemical separation is achieved through the wall or due to selective adsorption across the wall, thereby having analogy to a chromatographic process.

In both of the above embodiments, the housing may be made of any material such as metal, glass, plastic or wood, and may be of practically any dimension ranging from small to large. However, it is especially preferred if the desalination apparatuses of the present invention are of a size which is suitable for manual use by a human. Of course, by constructing the units from plastic, the units can be made having a light weight.

Moreover, a design may be used whereby two or more of the units are attached in sequence, whereby the effluent desalinated water from a first unit is fed into a second unit for further purification.

Finally, as noted, one of the present elastomeric-based mechanochemical machines may be used to prepare chemical gradients using pH systems or redox couples, for example as already mentioned. With the redox coupled, hemes, pyridine-flavin, pyridine-nucleotide or even quinone systems may be used. Generally, it is desirable to have a potential difference between redox states of at least 0.05 kcal/mole. On the other hand, potential difference of as high as 30 kcal/mole may be used.

Having now fully described this invention, it will be apparent to one of ordinary skill in the art that many changes and modifications can be made thereto without departing from the spirit or scope of the invention as set forth herein.

What is claimed is:

1. A mechanochemical device for desalinating sea water of brackish water by the conversion of mechanical work to chemical work, which comprises:
   a) a housing containing an elastomeric material capable of being stretched to thereby allow salt-diminished water to move into the elastomeric material while substantially repelling solvated salt ions from entry thereto,
   b) means for stretching and relaxing said elastomeric material in said housing, in connection with said elastomeric material; and
   c) means for uptake of said sea water or brackish water into said housing, means for draining concentrated saltwater from said housing, and means for draining desalinated water from said housing;
   wherein said elastomeric material is capable of reversibly contracting and relaxing by means of an inverse temperature transition wherein a change in chemical potential of a molecular species in solution will effect a change in said inverse temperature transition.

2. The mechanochemical device of claim 1, wherein said elastomeric matrix is cross-linked.

3. The mechanochemical device of claim 1, wherein said elastomeric material is in the form of a plurality of longitudinally-oriented elastomeric strips.

4. The mechanochemical device of claim 1, wherein said elastomeric material is in the form of a single elastomeric matrix in said housing.

5. The mechanochemical device of claim 1, wherein said housing is made of metal, glass, wood, rubber or plastic.

6. The mechanochemical device of claim 1, wherein said means for stretching and relaxing said elastomeric material in said housing is a manual plunger in connection with said elastomeric material.

7. The mechanochemical device of claim 1, wherein the elastomeric material comprises a sequential polypeptide having elastomeric repeating units comprising tetrapeptide or pentapeptide repeating units optionally modified by hexameric repeating units, and mixtures thereof, wherein said elastomeric repeating units comprise amino carboxylic acid residues selected from the group consisting of hydrophobic amino carboxylic acid and glycine residues and wherein said repeating units exist in a conformation having a β-turn.

8. The mechanochemical device of claim 7, wherein said repeating units comprises the formula -X$^1$-(IPGVG)$_n$-Y$^1$- and wherein I is a peptide-forming residue of L-isoleucine;
P is a peptide-forming residue of L-proline;
G is a peptide-forming residue of glycine;
V is a peptide-forming residue of L-valine;

and wherein X$^1$ is PGVG, GVG, VG, G or a covalent bond; Y$^1$ is IPGV, IPG, IP, or I or a covalent bond; and n is an integer from 1 to 200; or n is 0, with the proviso that X$^1$ and Y$^1$ together constitute a repeating pentapeptide unit.

9. The mechanochemical device of claim 7, wherein said repeating units comprises the formula -X$^2$-(VPGVG)$_n$-Y$^2$- and wherein P is a peptide-forming residue of L-proline;
G is a peptide-forming residue of glycine;
V is a peptide-forming residue of L-valine;

and wherein X$^2$ is PGVG, GVG, VG, G or a covalent bond; Y$^2$ is IPGV, IPG, IP, or I or a covalent bond; and n in both formulas is an integer from 1 to 200; or n is 0, with the proviso that X$^2$ and Y$^2$ together constitute a repeating pentapeptide unit.

10. The mechanochemical device of claim 7, wherein said repeating unit comprises the formula -X$^3$-(VPGG)$_n$-Y$^3$- and wherein P is a peptide-forming residue of L-proline;
G is a peptide-forming residue of glycine;
V is a peptide-forming residue of L-valine;

and wherein X$^3$ is PGG, GG, G or a covalent bond; Y$^3$ is VPG, VP, V or a covalent bond; and n is an integer from 1 to 200; or n is 0, with the proviso that X$^3$ and Y$^3$ together constitute a repeating tetrapeptide unit.

11. The mechanochemical device of claim 7, wherein said repeating unit comprises the formula -X$^4$-(IPGG)$_n$-Y$^4$- and wherein P is a peptide-forming residue of L-proline;
G is a peptide-forming residue of glycine;
I is a peptide-forming residue of L-isoleucine;

and wherein X$^4$ is PGG, GG, G or a covalent bond; Y$^4$ is IPG, IP, I or a covalent bond; and n is an integer from 1 to 200; or n is 0, with the proviso that X$^4$ and Y$^4$ together constitute a repeating tetrapeptide unit.

12. The mechanochemical device of claim 7, wherein said polypeptide comprises a mixture of repeating units.

13. The mechanochemical device of claim 7, wherein said repeating units comprise the formula (R$^1$PR$_2$R$_3$G)$_n$- or -(R$_1$PR$_2$R$_3$)n- or -(R$_1$PGG)$_n$- and wherein R$^1$ is selected from the group consisting of Phe, Leu, Ile, and Val; R$_2$ is selected from the group consisting of Ala and Gly; R$_3$ is selected from the group consisting of Phe, Leu, Ile, and Val; n is an integer from 1 to 200; and P is L-proline and G is glycine.

14. The mechanochemical device of claim 7, wherein said hydrophobic amino carboxylic acid residues are selected from the group consisting of residues of hydrophobic α-amino carboxylic acids.

15. The mechanochemical device of claim 7, wherein said hydrophobic amino carboxylic acid residues are selected from the group consisting of alanine, valine, leucine, isoleucine, and proline.

16. The mechanochemical device of claim 7, wherein said polypeptide comprises a combination of the repeating units -αPσΩG- or (VPφδ)$_n$- wherein V is a peptide-forming residue of L-valine;
P is a peptide-forming residue of L-proline;
G is a peptide-forming residue of glycine;
α is a peptide-forming residue of L-valine or a peptide-forming residue of L-Glu, L-Asp, L-His, L-Lys, L-Tyr, or another ionizable peptide-forming L-amino acid residue;
σ is a peptide-forming residue of glycine or a peptide-forming residue of D-Glu, D-Asp, D-His, D-Lys, D-Tyr, or another ionizable peptide-forming D-amino acid residue; and
Ω is a peptide-forming residue of L-valine or a peptide-forming residue of L-Glu, L-Asp, L-His, L-Lys, L-Tyr, or another ionizable peptide-forming L-amino acid residue; and
φ is a peptide-forming residue of D-Glu, D-Asp, D-His, D-Lys, D-Tyr, or another ionizable peptide-forming D-amino acid residue; and
δ is a peptide-forming residue of L-Glu, L-Asp, L-His, L-Lys, L-Tyr or another ionizable peptide-forming L-amino acid residue; and
n is an integer of from 1 to 5,000.

17. The mechanochemical device of claim 7, wherein said repeating units are of the general formula -(S$_a$-T$_b$)-n wherein either S or T comprise a functional repeating unit designed to modify or shift the temperature of elastomeric force development of the elastomeric material, while either S or T, whichever is remaining, comprises another repeating unit of the elastomeric material, and a, b, and n are integers.

18. The mechanochemical device capable of utilizing mechanical work to produce chemical gradients, which comprises:

a) a housing containing an elastomeric material capable of reversibly contracting and relaxing by chemical modulation of an inverse temperature transition, and containing a chemical functionality capable of existing in either of two states, wherein said state determines the temperature of the inverse temperature transition;

b) means for stretching and relaxing said elastomeric material in said housing, in connection with said elastomeric material; and c) means for uptake of a solution into said housing, means for draining concentrated solution or chemical species contained in said feed solution from said housing, and means for draining solution from said housing which is less concentrated with respect to the chemical species than that contained in said feed solution.

* * * * *